US008591540B2

(12) United States Patent
Boyle et al.

(10) Patent No.: US 8,591,540 B2
(45) Date of Patent: Nov. 26, 2013

(54) EMBOLIC FILTERING DEVICES

(75) Inventors: William J. Boyle, Fallbrook, CA (US); John E. Papp, Temecula, CA (US); Charles R. Peterson, Murrieta, CA (US); Paul F. Muller, San Carlos, CA (US); Donald Schwarten, Saratoga, CA (US); Kathern J. Lind, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1520 days.

(21) Appl. No.: 10/675,611

(22) Filed: Sep. 29, 2003

(65) Prior Publication Data

US 2005/0004595 A1      Jan. 6, 2005

Related U.S. Application Data

(63) Continuation-in-part of application No. 10/377,285, filed on Feb. 27, 2003, now abandoned.

(51) Int. Cl.
*A61M 29/00*      (2006.01)

(52) U.S. Cl.
USPC ........................................................ 606/200

(58) Field of Classification Search
USPC ........................................................ 606/200
See application file for complete search history.

(56) References Cited

U.S. PATENT DOCUMENTS 3,459,184 A * 8/1969 Ring .................. 604/164.08
3,952,747 A    4/1976 Kimmell, Jr.
4,425,908 A    1/1984 Simon
4,494,531 A    1/1985 Gianturco
4,612,931 A    9/1986 Dormia
(Continued)

FOREIGN PATENT DOCUMENTS

EP      0427429 A3      9/1991
EP      0472334 A1      2/1992
(Continued)

OTHER PUBLICATIONS

Dilitation of the Carotid Artery by a Temporary Carotid Filter by A. Beck, St. Milic, A.M. Spagnoli, November-December Issue of OPLITAI, An International Journal on Military Medicine and Health Emergencies, pp. 67-74.
(Continued)

*Primary Examiner* — Thomas J Sweet
*Assistant Examiner* — Christopher D Prone
(74) *Attorney, Agent, or Firm* — Jonathan F. Feuchtwang; Fulwider Patton LLP

(57) ABSTRACT

An embolic filtering system includes a guide wire, a filter device disposed on the guide wire, a sheath adapted to maintain the filter device in an unexpanded position and a torque device having a lumen for receiving the guide wire and a locking mechanism for locking the torque device to the guide wire. The torque device may include a side port adapted to receive the proximal end of the sheath to allow a portion of the guide wire to shear the sheath from the guide wire through retraction of the sheath through the side port. The torque device may include an extension arm having a distal opening adapted to receive both the guide wire and the sheath. A second lumen may be used to allow a portion of the guide wire to shear the sheath away from the guide wire through retraction of the sheath through the second lumen.

24 Claims, 15 Drawing Sheets

(56) References Cited

U.S. PATENT DOCUMENTS

| | | |
|---|---|---|
| 4,616,653 A | 10/1986 | Samson et al. |
| 4,619,246 A | 10/1986 | Molgaard-Nielsen et al. |
| 4,619,263 A | 10/1986 | Frisbie et al. |
| 4,619,274 A | 10/1986 | Morrison |
| 4,643,184 A | 2/1987 | Mobin-Uddin |
| 4,650,466 A | 3/1987 | Luther |
| 4,662,885 A | 5/1987 | DiPisa, Jr. |
| 4,664,113 A | 5/1987 | Frisbie et al. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,748,982 A | 6/1988 | Horzewski et al. |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,801,294 A * | 1/1989 | Okada .................. 604/171 |
| 4,832,055 A | 5/1989 | Palestrant |
| 4,873,978 A | 10/1989 | Ginsburg |
| 4,887,997 A * | 12/1989 | Okada .................. 604/516 |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,161,534 A * | 11/1992 | Berthiaume .................. 600/434 |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,662,703 A | 9/1997 | Yurek et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A * | 11/2000 | Broome et al. ............ 606/200 |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,228,062 B1 * | 5/2001 | Howell et al. ............ 604/171 |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,251,122 B1 | 6/2001 | Tsukernik |
| 6,254,633 B1 | 7/2001 | Pinchuk et al. |
| 6,258,115 B1 | 7/2001 | Dubrul |

(56) References Cited

U.S. PATENT DOCUMENTS

| | | | |
|---|---|---|---|
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,364,900 B1 | 4/2002 | Heuser |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 * | 9/2003 | Thielen .................... 606/200 |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |

(56) References Cited

U.S. PATENT DOCUMENTS

| | | |
|---|---|---|
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boylan et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salahieh et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan et al. |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi et al. |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Peterson |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Papp et al. |
| 7,097,651 B2 | 8/2006 | Harrison et al. |
| 7,101,380 B2 | 9/2006 | Khachin et al. |
| 7,108,707 B2 | 9/2006 | Huter et al. |
| 2002/0022858 A1 | 2/2002 | Demound et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133092 A1 | 9/2002 | Oslund et al. |
| 2002/0138094 A1 | 9/2002 | Borillo et al. |
| 2002/0138095 A1 | 9/2002 | Mazzocchi et al. |
| 2002/0143360 A1 | 10/2002 | Douk et al. |
| 2002/0143361 A1 | 10/2002 | Douk et al. |
| 2002/0151927 A1 | 10/2002 | Douk et al. |

(56) References Cited

U.S. PATENT DOCUMENTS

| | | |
|---|---|---|
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0097095 A1 | 5/2003 | Brady et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Brady et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kasleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Esksuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082697 A1 | 4/2004 | Broome et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |

(56) References Cited

U.S. PATENT DOCUMENTS

| | | |
|---|---|---|
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahieh |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salahieh et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0533511 A1 | 3/1993 |
| EP | 1 127 556 A2 | 8/2001 |
| EP | 1 127 556 A3 | 8/2001 |
| FR | 2580504 A1 * | 10/1984 |
| FR | 2580504 A1 | 10/1986 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |

(56) References Cited

FOREIGN PATENT DOCUMENTS

| WO | WO98/33443 | 8/1998 |
|----|------------|--------|
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO02/28292 | 4/2002 |
| WO | WO2004/021928 | 3/2004 |

OTHER PUBLICATIONS

Minibasket for Percutaneous Embolectomy and Filter Protection Against Distal Embolization: Technical Note.

* cited by examiner

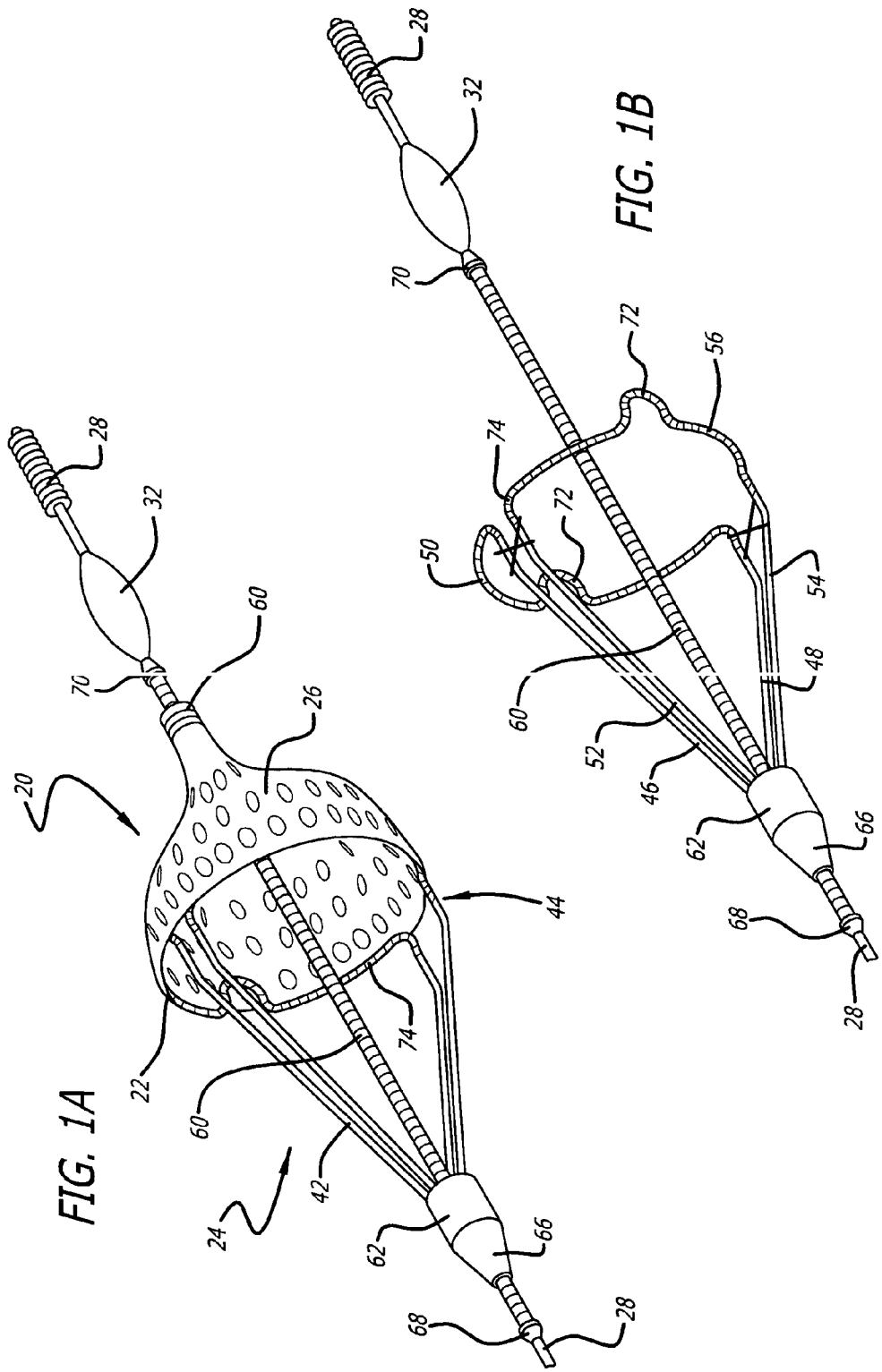

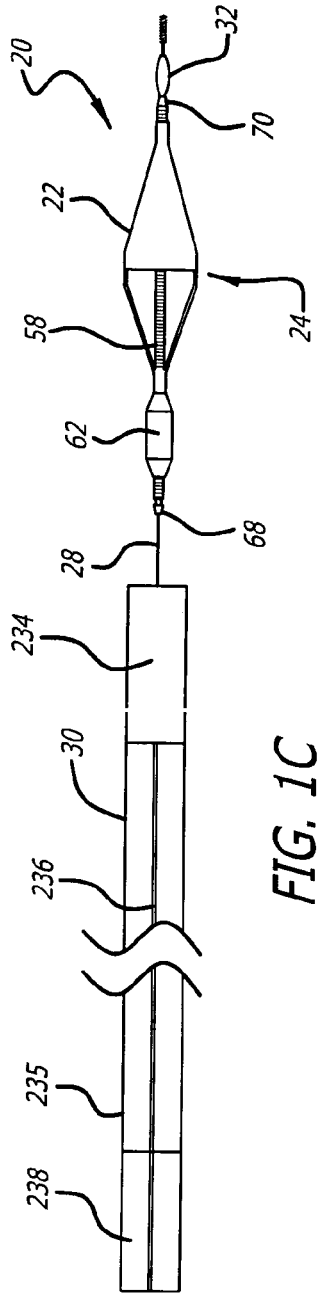
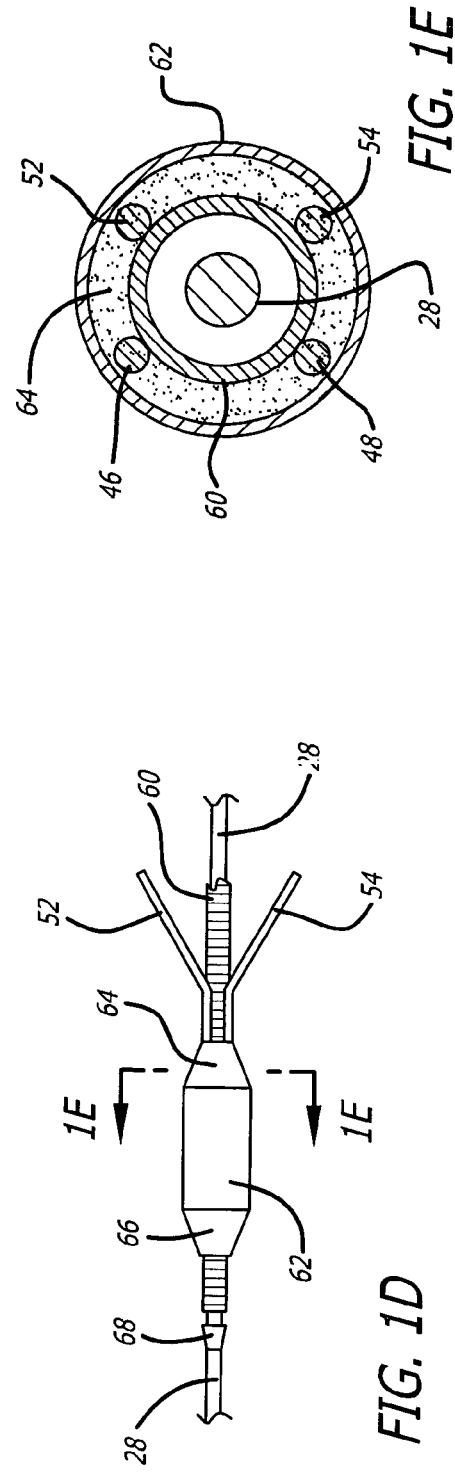

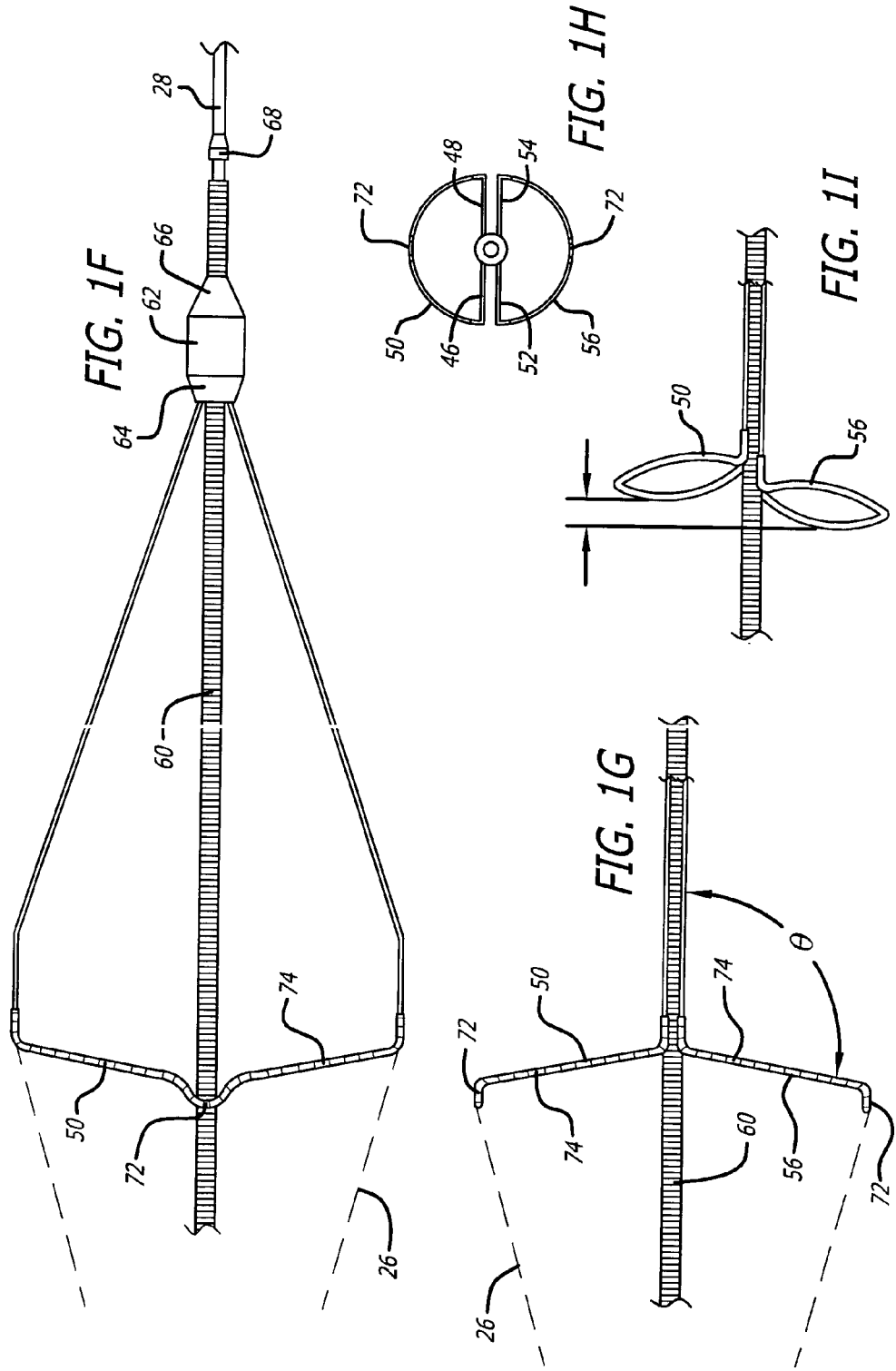

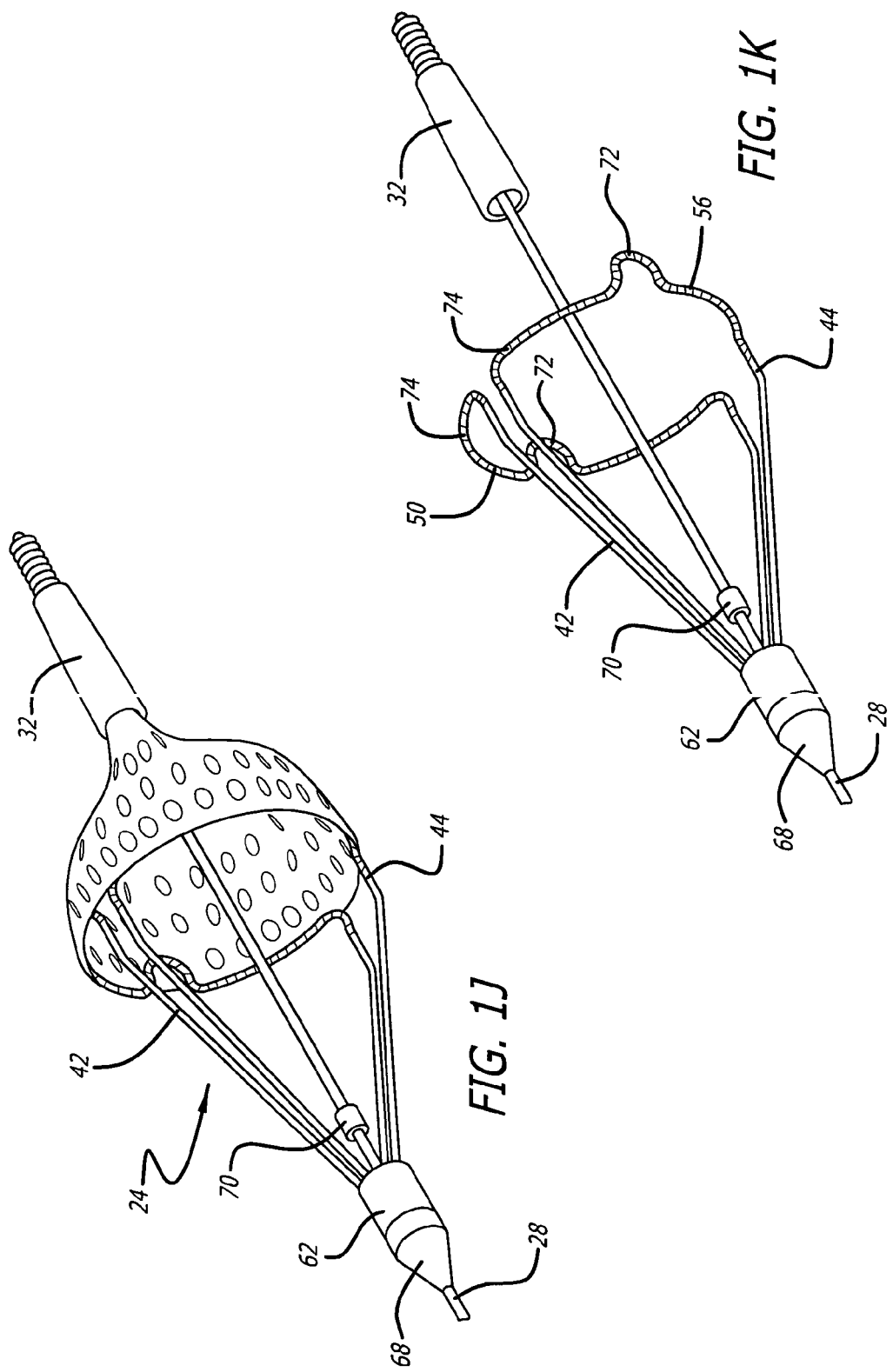

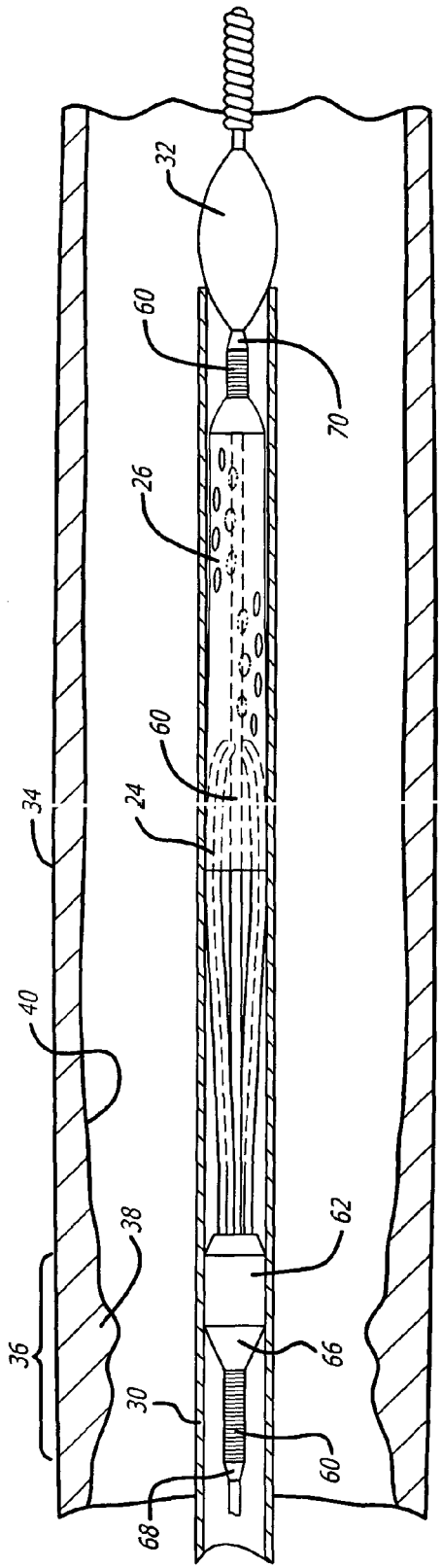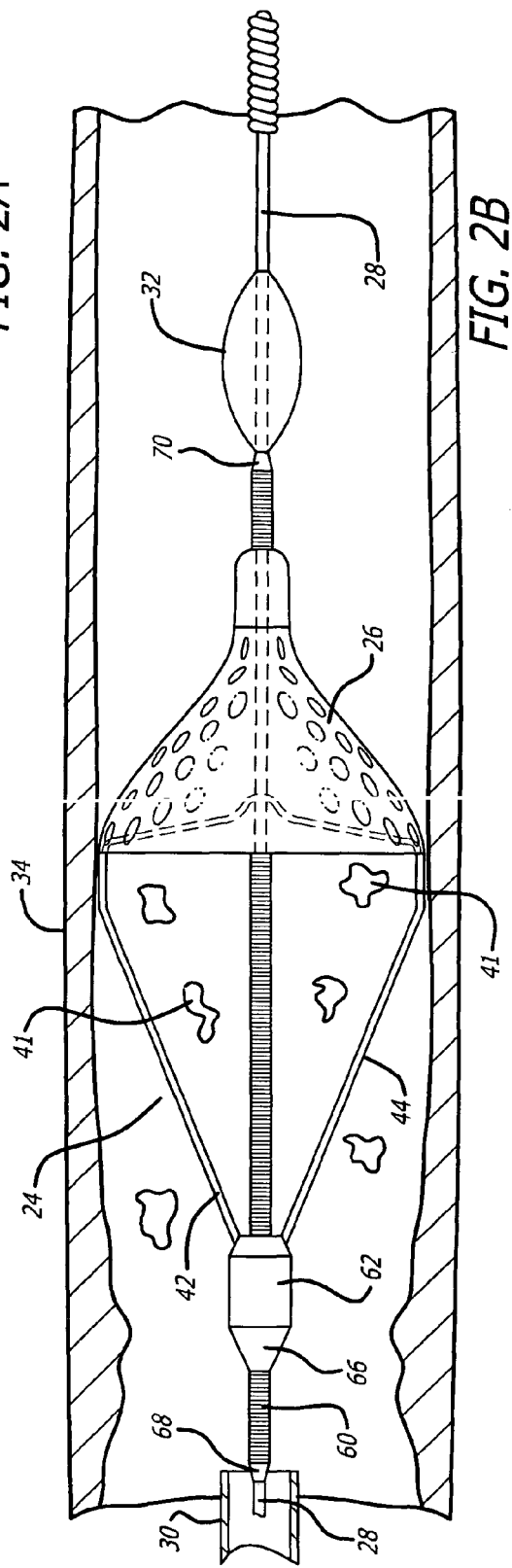

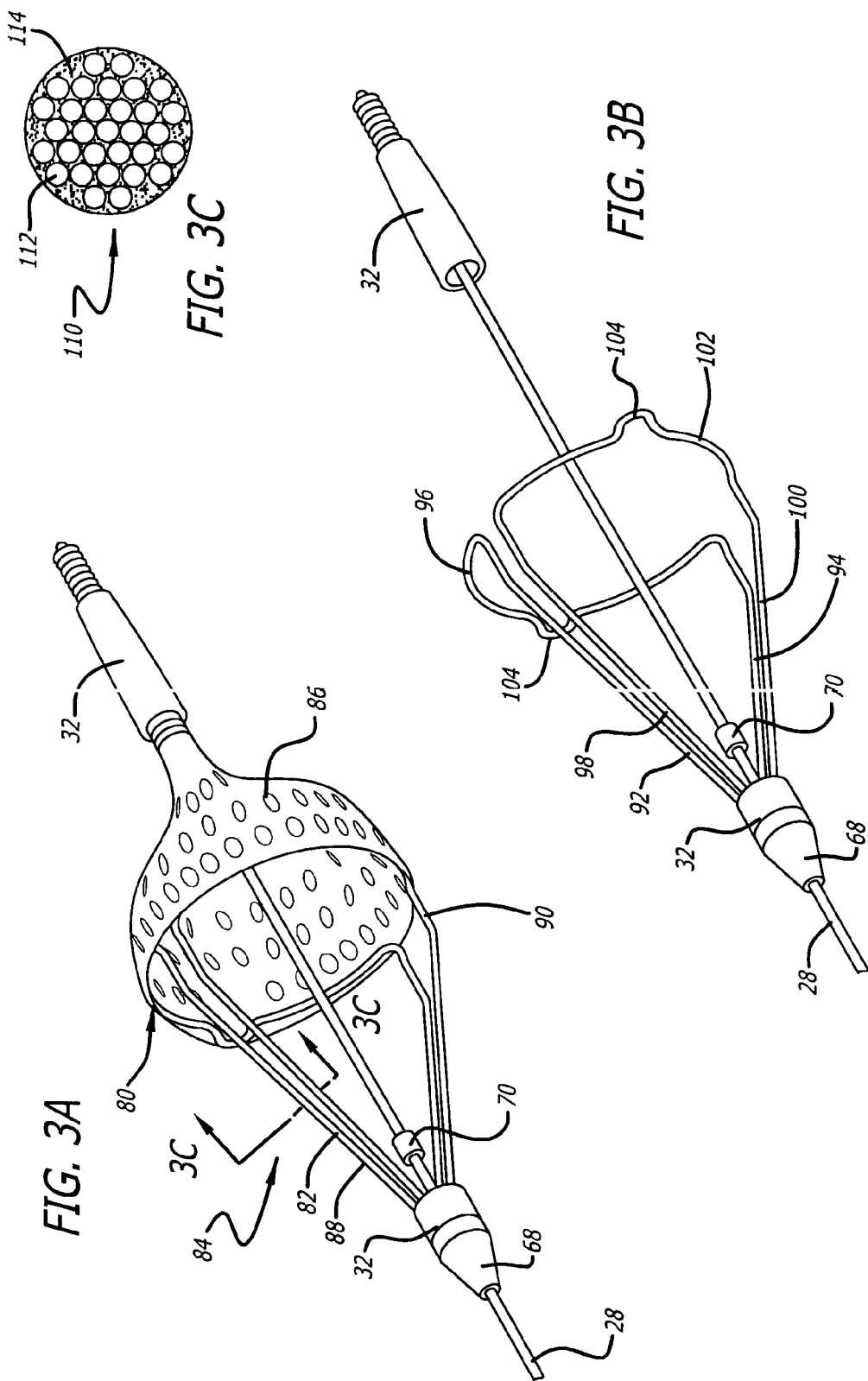

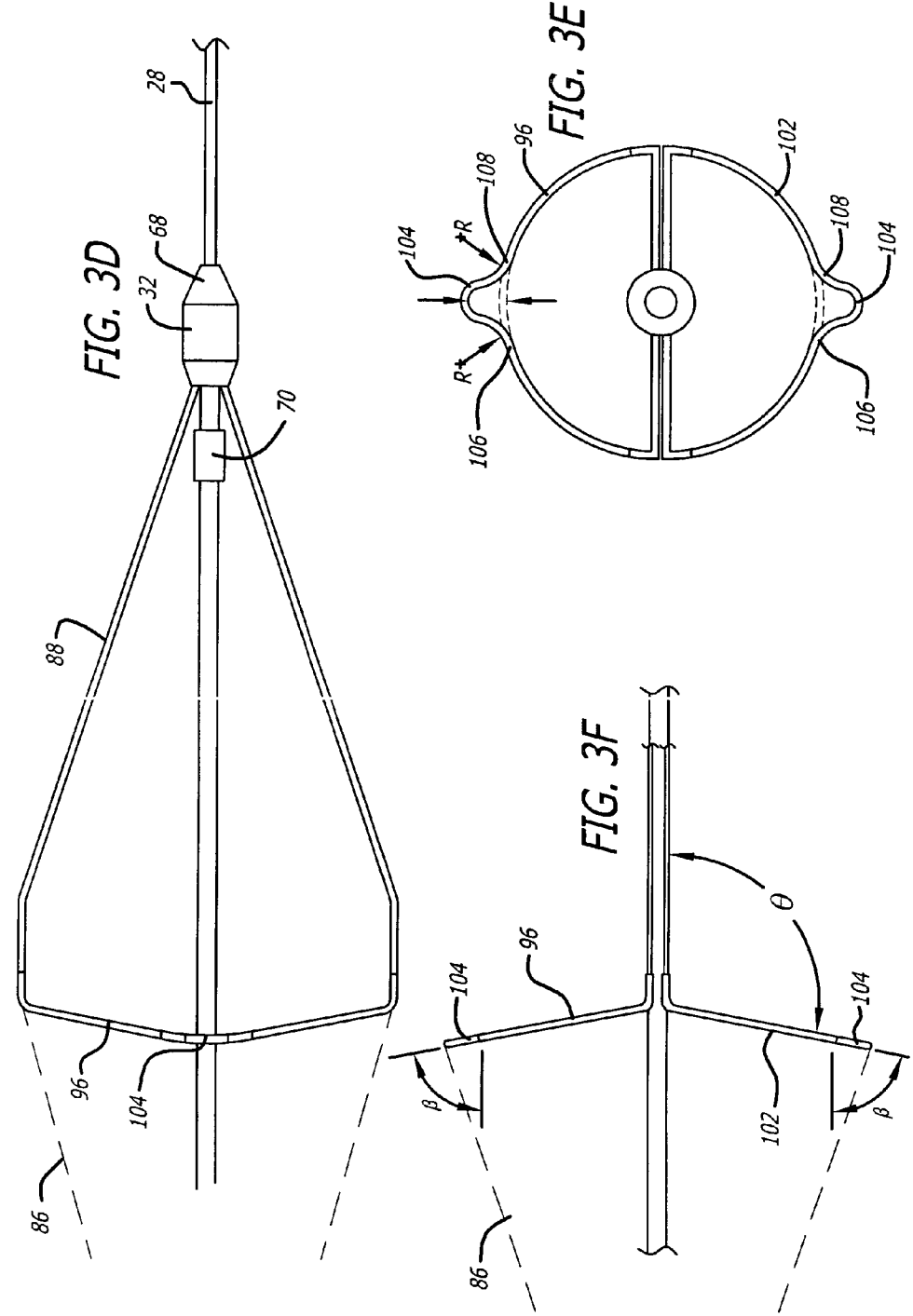

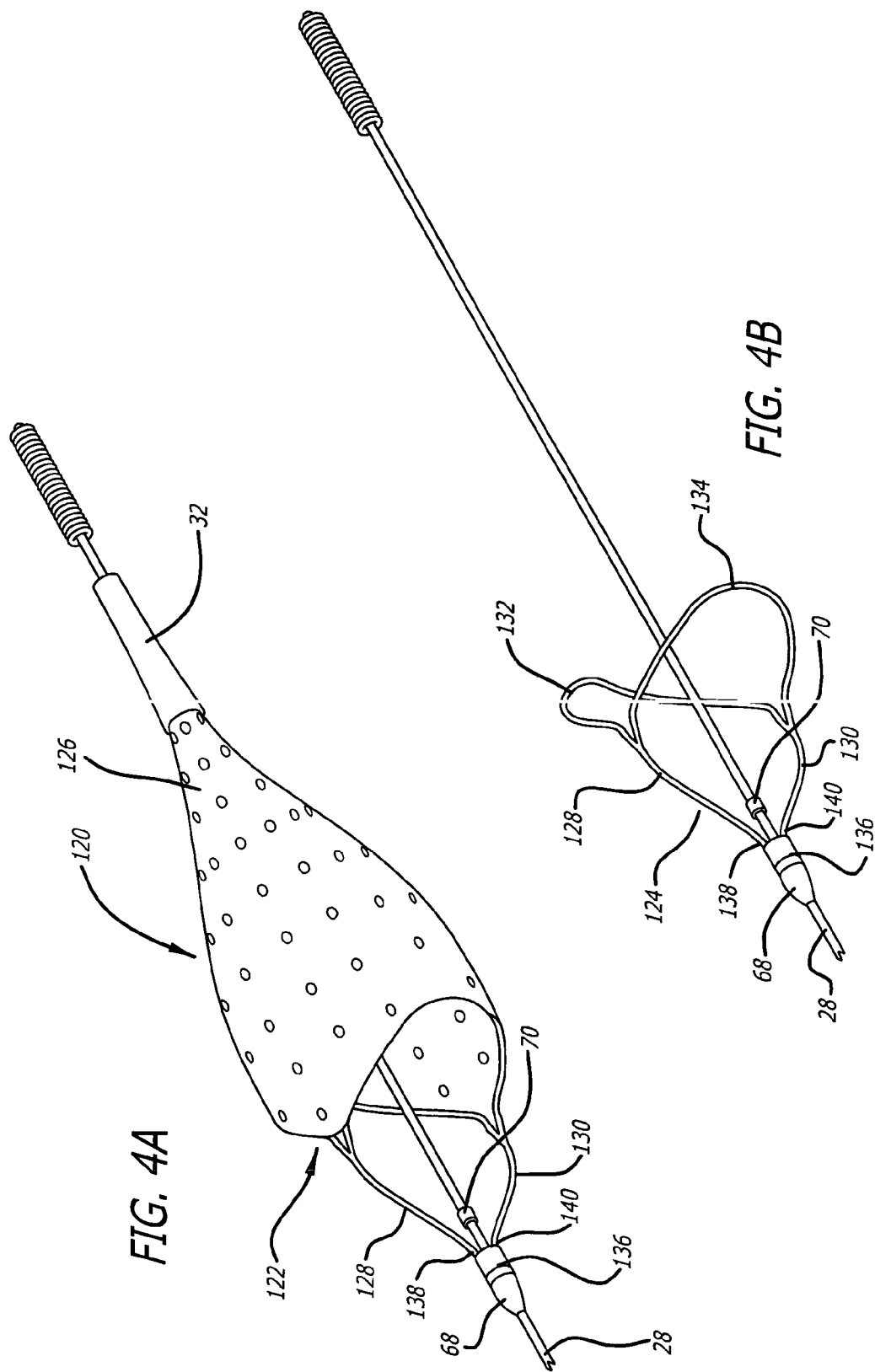

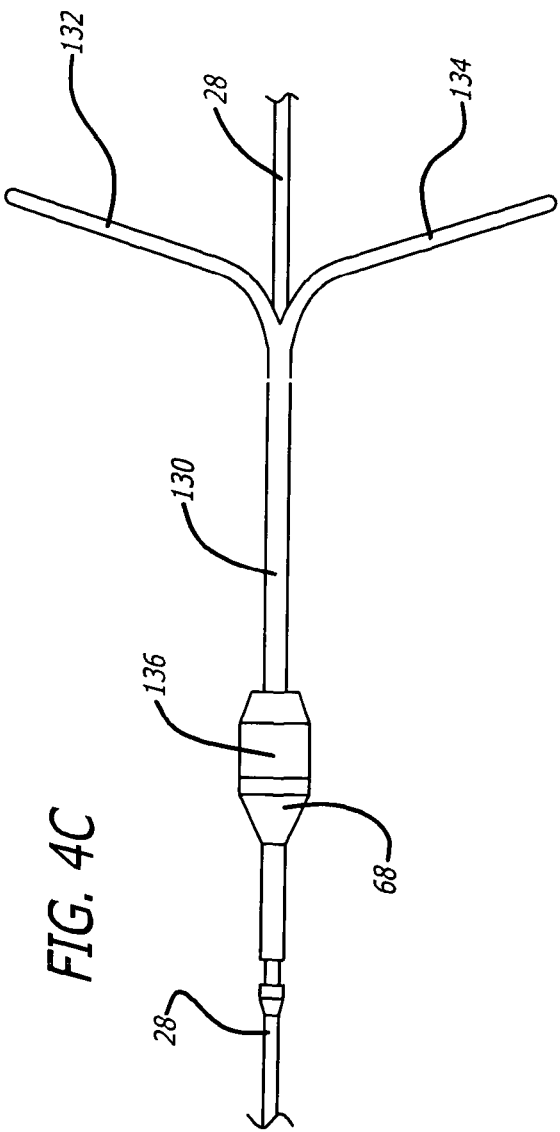
FIG. 4C
FIG. 5C
FIG. 5D

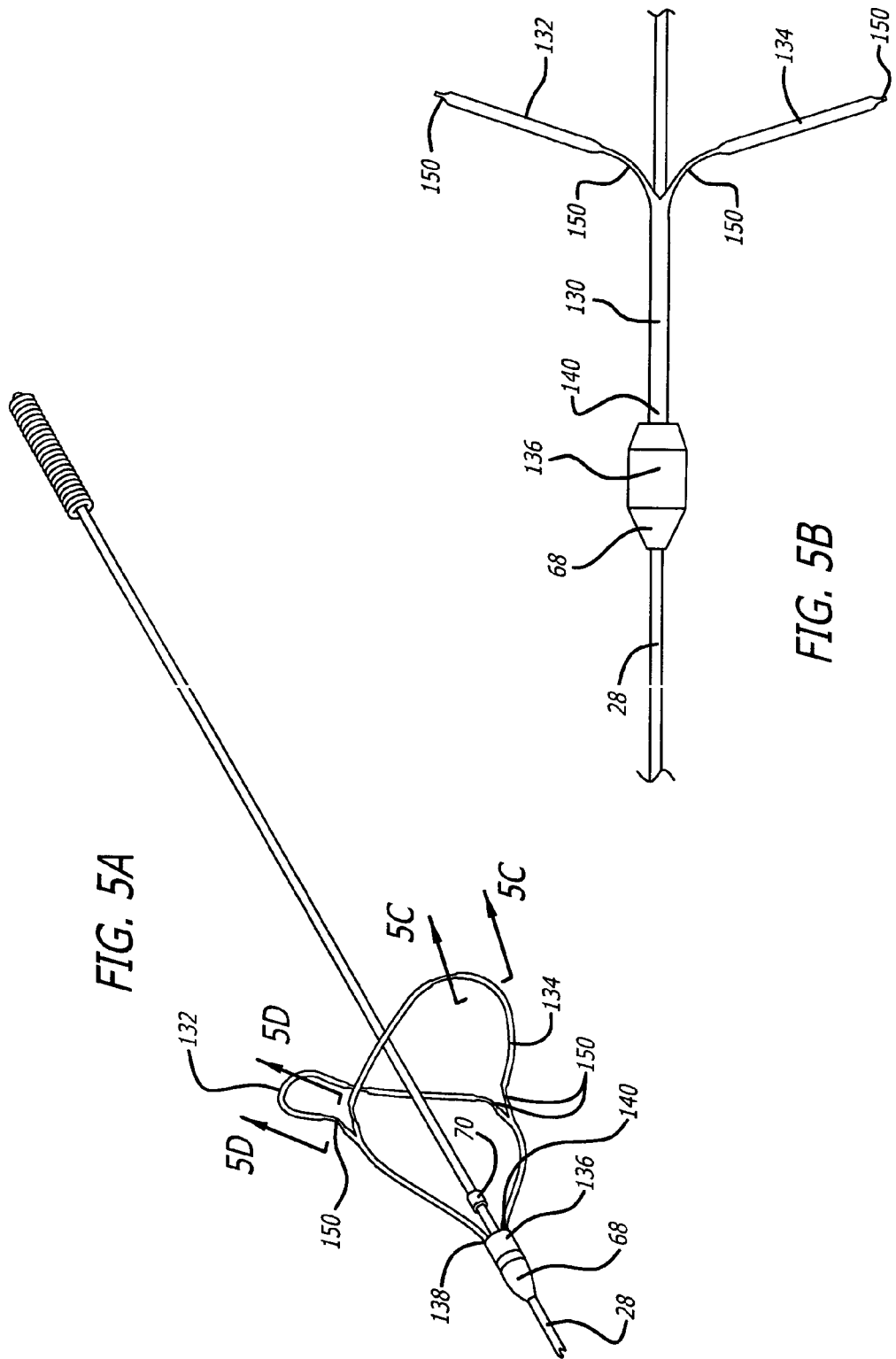

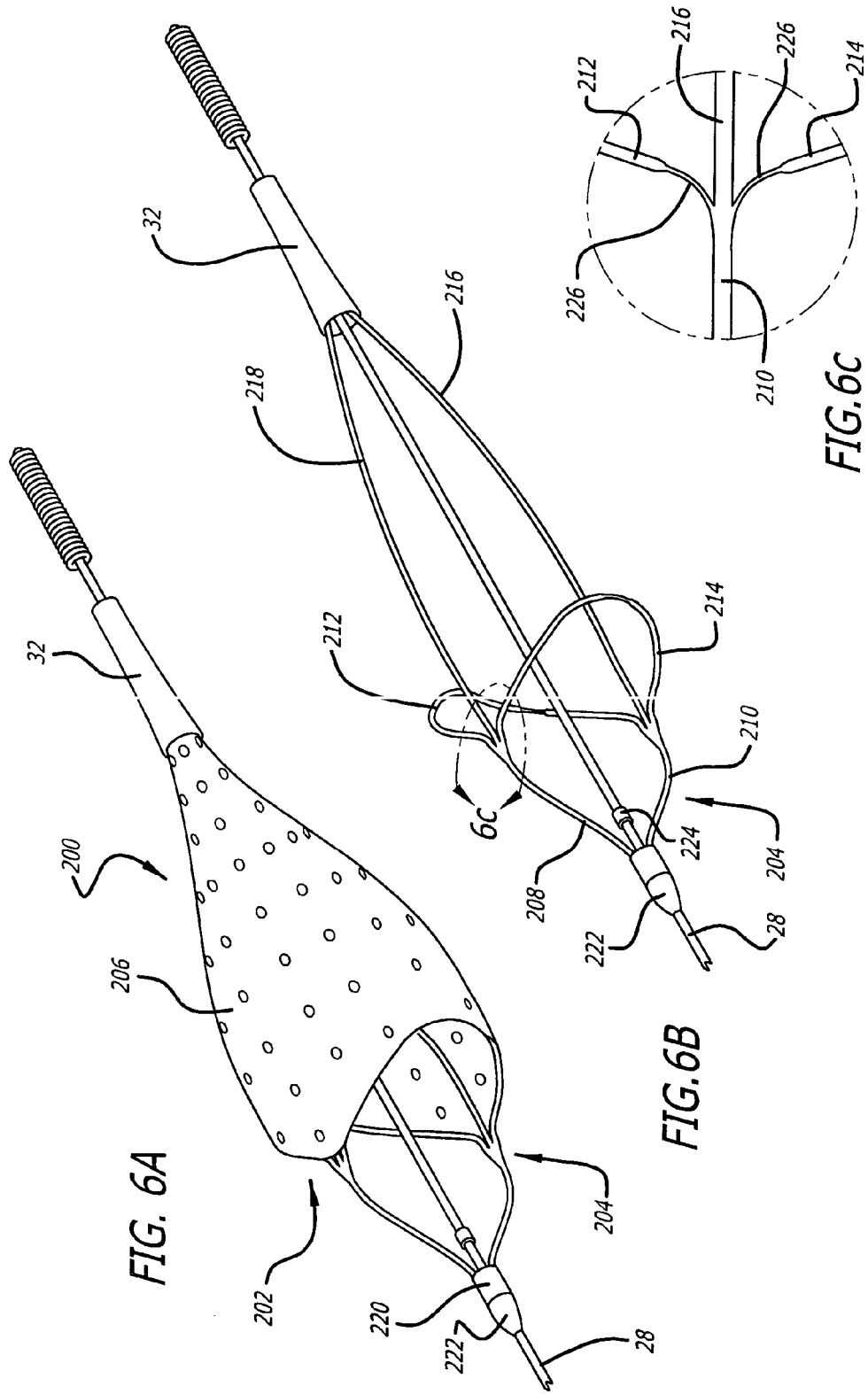

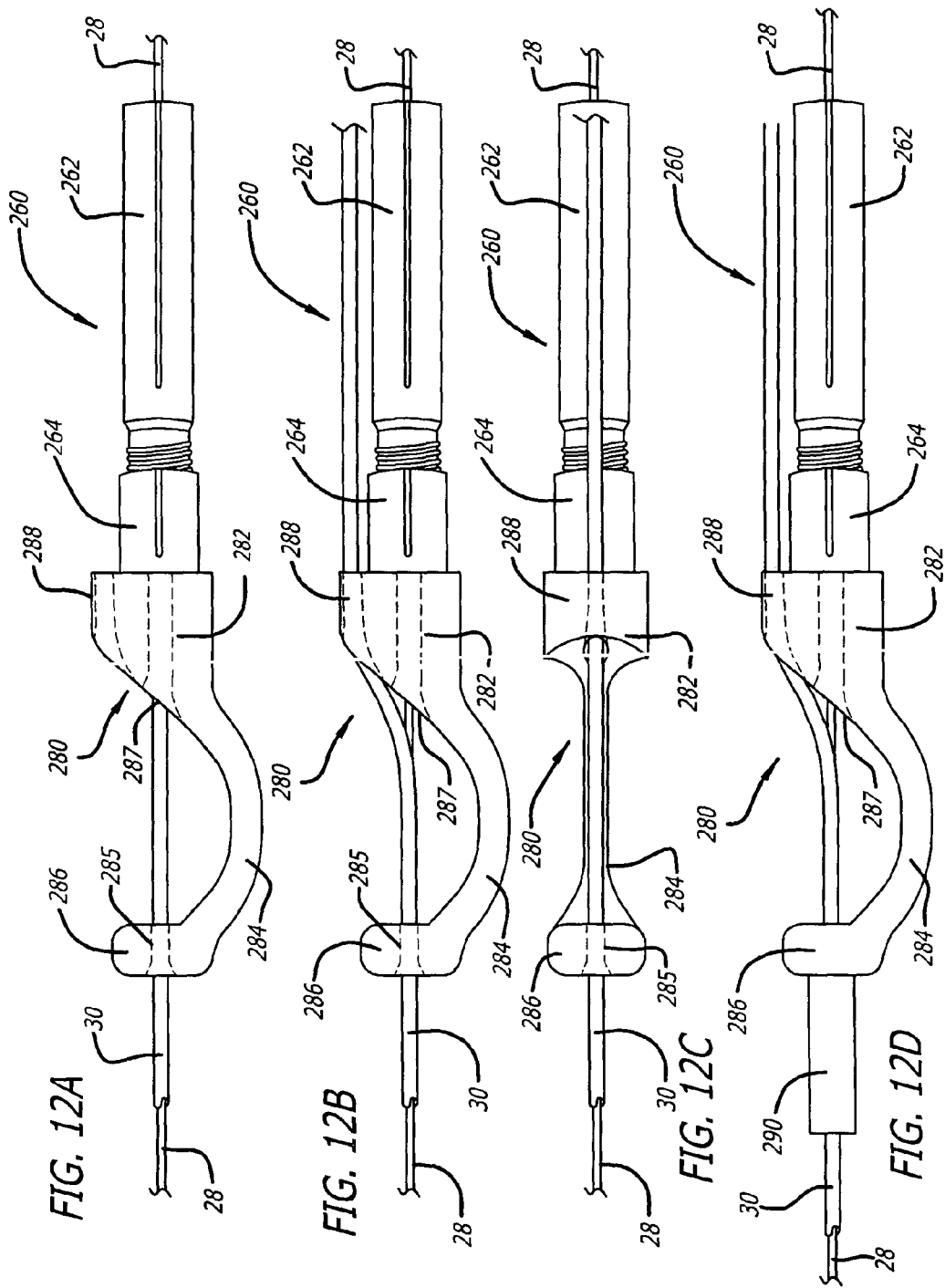

EMBOLIC FILTERING DEVICES

CROSS-REFERENCE TO RELATED APPLICATION

This application is a continuation-in-part of application Ser. No. 10/377,285 filed Feb. 27, 2003, now abandoned which is assigned to the same Assignee as the present application.

BACKGROUND OF THE INVENTION

The present invention relates generally to filtering devices and systems which can be used, for example, when an interventional procedure is being performed in a stenosed or occluded region of a body vessel to capture embolic material that may be created and released into the body fluid during the procedure. The present invention is more particularly directed to an embolic filtering device made with a self-expanding frame (also referred to as a basket or cage) having good flexibility and bendability to reach often tortuous areas of treatment, along with special torque devices that are used to facilitate the rapid removal of a peel-away delivery sheath used to position the filtering device within the patient's vasculature.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A catheter is usually used to capture the shaved plaque or thrombus from the bloodstream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. This is particularly true when the procedure is performed in a saphenous vein graft (SVG). Additionally, while complete vaporization of plaque is the intended goal during laser angioplasty, sometimes particles are not fully vaporized and enter the bloodstream. Likewise, not all of the emboli created during an atherectomy procedure may be drawn into the catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, the expandable filter portion should remain flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when deploying the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Expandable filters can be provided with some increased flexibility by forming the struts of the filter assembly from relatively thin material. However, the use of thin material often can reduce the radiopacity of the expandable filter, often making it difficult for the physician to visualize the filter during deployment. Visualization of filters made from a nickel-titanium alloy, which has relatively low radiopacity as compared to other metallic materials, is also difficult during fluoroscopy. Conversely, the use of thicker materials, which can promote radiopacity of the expandable filter, usually reduces its flexibility, which may impair the deliverability of the expandable filter within the patient.

What has been needed is an expandable filter assembly having high flexibility with sufficient strength and radiopacity to be successfully deployed within a patient's vasculature to collect embolic debris which may be released into the patient's vasculature. The present invention disclosed herein satisfies these and other needs.

SUMMARY OF THE INVENTION

The present invention provides a flexible self-expanding frame for use with an embolic filtering device designed to capture embolic debris created during the performance of a therapeutic interventional procedure, such as a balloon angioplasty or stenting procedure, in a body vessel. The present invention provides the physician with an embolic filtering device having the flexibility needed to be steered through tortuous anatomy, but yet possesses sufficient strength to hold open a filtering element against the wall of the body vessel for capturing embolic debris. The present invention provides sufficient flexibility without compromising the radiopacity characteristics of the filtering device. An embolic filtering device made in accordance with the present invention is relatively easy to deploy and has good flexibility and conformability to the patient's anatomy.

An embolic filter assembly of the present invention utilizes an expandable frame made from a self-expanding material, for example, linear pseudoelastic nickel-titanium (NiTi). In some aspects of the present invention, the frame is made from a pair of half frames capable of expanding from an unexpanded position having a first delivery diameter to an expanded or deployed position having a second expanded diameter. A filter element made from an embolic-capturing material is attached to the expandable frame to move between the unexpanded position and deployed position.

The half frames which cooperatively form the expandable frame can be set to remain in the expanded, deployed position until an external force is placed over the half frames to collapse and move the frames to the unexpanded position. One way of accomplishing this is through the use of a restraining sheath, for example, which can be placed over the filtering device in a coaxial fashion to contact the half frames and move the half frames into the unexpended position. The embolic filtering device can be attached to the distal end of an elongated member, such as a guide wire, for temporary placement in the vasculature. A guide wire may be used in conjunction with the filtering device when embolic debris is to be filtered during, for example, an interventional procedure. In this manner, the guide wire and filtering assembly, with the restraining sheath placed over the filter assembly, can be placed into the patient's vasculature. Once the physician properly manipulates the guide wire into the target area, the restraining sheath can be retracted to deploy the expandable frame into the expanded position. This can be easily performed by the physician by simply retracting the proximal end of the restraining sheath (located outside of the patient). Once the restraining sheath is retracted, the self-expanding properties of the frame cause each half frame to move in an outward, radial fashion away from the guide wire to contact the wall of the body vessel. As the half frames expand radially, so does the filter element which will now be maintained in place to collect embolic debris that may be released into the bloodstream as the physician performs the interventional procedure. The guide wire is used by the physician to deliver the necessary interventional device into the area of treatment. The deployed filter element captures any embolic debris created and released into the body vessel during the procedure.

In some aspects, the present invention is directed to improvements relating to the mounting and positioning of the pair of half frames which cooperatively form the expandable frame of the embolic filter assembly. In one particular aspect of the present invention, each of the half frames includes a first control arm connected to a second control arm by a partial loop. The partial loop extends radially outward when placed in an expanded position so that a substantially circular loop is created by the two partial loops. The partial loops may include an articulation region which helps to distribute strain which can be developed when the half frame move between the expanded and collapsed positions. The articulation region also enhances the bendability of the half frames. In one particular embodiment, the articulation region can take on a D-shaped curve which extends from the apex of the partial loop. The placement and angulation of the articulation region on the partial loops can be varied to achieve the desired amount of bending and flexibility needed for a particular material or wire diameter.

In another aspect of the present invention, the half frames can be mounted onto a filter support structure which allows the composite frame and filter element to rotate relative to the guide wire without twisting the filter. In one particular aspect, the filter support structure can be a coiled wire which provides excellent bendability to the assembly of components. The filter support structure can be mounted between a pair of fittings located on the guide wire which limit or eliminate relative longitudinal movement between the filter assembly and the guide wire.

In another aspect of the present invention, the frame includes a first and a second control arm which are attached to a pair of partial loops that expand to form a composite circular loop for maintaining the filter element in position against the wall of the body vessel. The pair of partial loops can include articulation regions and strain distributing struts which increase flexibility and bendability at various bend points on the frame. In a variation of this frame, a set of distal control arms can extend from the connection of the first and second control arms and the partial loops to a distal mounting region. This second set of distal control arms can support the filter element and help prevent the filter element from rotating differently, i.e. twisting, to that of the frame.

In another aspect of the present invention, the frame can be made from linear, pseudoelastic Nitinol which imparts a shape setting without eventually developing stress-induced martensite. This is one of the particular materials that could be used to manufacture the half frames and composite frames of the present invention.

In another aspect of the present invention, a special torque device can be utilized in conjunction with a peel-away delivery sheath which is utilized to deliver the collapsed embolic filter assembly into the patient's vasculature. The special torque device includes a side port for receiving the proximal end of the delivery sheath through which the physician pulls the sheath to cause the sheath to be split by the guide wire. As a result, the delivery sheath can be quickly and easily removed from the guide wire once the embolic filtering assembly has been positioned in the target location in the patient. One embodiment of the special torque device is a clip-on component which can be attached to a conventional torque device and includes a side port that causes the delivery sheath to be split as it is being removed from the guide wire. In another aspect of the torque device, an arm extension helps to maintain the delivery sheath on the guide wire along the same axis until the delivery sheath is placed in a side port located on the device. The extension arm helps to prevent "splaying" and kinking of the guide wire as the delivery sheath is being "stripped" or "peeled" from the guide wire.

The present invention is particularly useful when an interventional procedure, such as balloon angioplasty, stenting procedure, laser angioplasty or atherectomy, is being performed in a critical body vessel, such as the carotid arteries, where the release of embolic debris into the bloodstream can occlude the flow of oxygenated blood to the brain, resulting in grave consequences to the patient. While the present invention is particularly useful in carotid procedures, the invention can be used in conjunction with any vascular procedure in which embolic risk is present. Also, it is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1A is a perspective view of an embolic filtering device embodying features of the present invention.

FIG. 1B is a perspective view of the embolic filtering device of FIG. 1A shown without the filter element attached to the expandable frame.

FIG. 1C is a side elevational view of an embolic filtering system which includes the embolic filtering device of FIG. 1A and a delivery sheath.

FIG. 1D is a side elevational view of the proximal end of the embolic filtering device of FIG. 1A showing in greater detail the mounting of the pair of half frames to the filter coil.

FIG. 1E is a cross-sectional view taken along line 1E-1E from FIG. 1D.

FIG. 1F is a top plan view of the expandable frame device of FIG. 1B which shows the D-shaped articulation region formed on the half frame.

FIG. 1G is a side elevational view of the expandable frame of FIG. 1B which shows the positioning of the half frames in an expanded position.

FIG. 1H is an end view which shows the expanded half frames that form the expandable frame of the embolic filtering device of FIGS. 1A and 1B.

FIG. 1I is a side elevational view showing an offset positioning of half frames forming the expandable frame.

FIG. 1J is a perspective view of the expandable frames and filter element of FIGS. 1A and 1B and an alternative way to mount the filtering assembly to a guide wire.

FIG. 1K is a perspective view of the embolic filtering device of FIG. 1J shown without the filter element attached to the expandable frame.

FIG. 2A is a side elevational view, partially in cross-section, of the embolic filtering system shown in FIG. 1C as it is being delivered within a body vessel.

FIG. 2B is a side elevational view, partially in cross section, similar to that shown in FIG. 2A, wherein the embolic filtering device is deployed in its expanded, implanted position within the body vessel.

FIG. 3A is a perspective view of another embodiment of an embolic filtering device embodying features of the present invention.

FIG. 3B is a side elevational view of the embolic filtering device of FIG. 3A shown without the filter element attached to the half frames which form the expandable frame.

FIG. 3C is a cross-sectional view showing a stranded wire encapsulated by a layer of polymeric material which can be used to form the frames of any of the embolic filtering devices made in accordance with the present invention.

FIG. 3D is a top plan view showing one of the half frames of FIGS. 3A and 3B in an expanded position.

FIG. 3E is an end view showing the expanded half frames which form the expandable frame of the filtering of device of FIGS. 3A and 3B.

FIG. 3F is a side elevational view showing the two half frames which form the expandable frame of the embolic filtering device shown in FIG. 3B in the expanded position.

FIG. 4A is a perspective view of another embodiment of an embolic filtering device embodying features of the present invention.

FIG. 4B is a perspective view of the embolic filtering device of FIG. 4B shown without the filter element attached to the expandable frame.

FIG. 4C is a side elevational view of the expandable frame shown in FIG. 4B.

FIG. 5A is a perspective view of an embolic filtering device (without filter element) which embodies features of the present invention.

FIG. 5B is a side elevational view of the embolic filtering device (without filter element) of FIG. 5A in its expanded position.

FIG. 5C is a cross-sectional view taken along lines 5C-5C.

FIG. 5D is a cross-sectional view taken along lines 5D-5D.

FIG. 6A is a perspective view of another embodiment of an embolic filtering device embodying features of the present invention.

FIG. 6B is a perspective view of the embolic filtering device of FIG. 6A shown without the filter element attached to the expandable frame.

FIG. 6C is an enlarged view which shows the connection of the control arms and partial loop which form the expandable frame shown in FIG. 6B.

FIG. 12A is a side elevational view of another embodiment of a torque device having a side port which can be used to peel away the delivery sheath, similar to the one shown in FIG. 7.

FIG. 12B is a side elevational view of the torque device of FIG. 12A showing the delivery sheath being peeled away from the guide wire.

FIG. 12C is a top view of the torque device of FIG. 12B.

FIG. 12D is a side elevational view of a modified embodiment of the torque device of FIG. 12A.

DETAILED DESCRIPTION OF THE PREFERRED EMBODIMENTS

Figure 7:
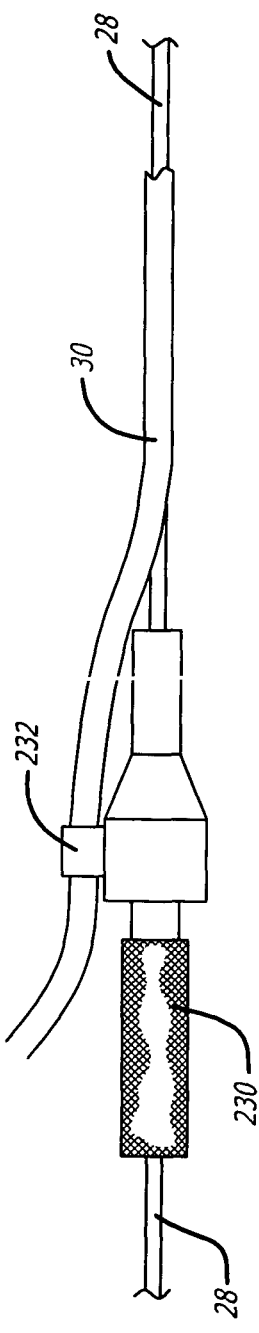
FIG. 7 is a side elevational view of a torque device having a side port which can be used to peel away the delivery sheath, as is shown in FIG. 1C after the filtering assembly has been deployed within a patient's vasculature.

Turning now to the drawings, in which like reference numerals represent like or corresponding elements in the drawings, FIGS. 1A, 1B and 1C illustrate one particular embodiment of an embolic filtering device 20 incorporating features of the present invention. This embolic filtering device 20 is designed to capture embolic debris which may be created and released into a body vessel during, for example, an interventional procedure. The embolic filtering device 20 includes an expandable filter assembly 22 having a self-expanding frame 24 (also referred to as a basket) and a filter element 26 attached thereto. In this particular embodiment, the expandable filter assembly 22 is rotatably mounted near the distal end of an elongated tubular or solid shaft, such as a steerable guide wire 28. A restraining or delivery sheath 30 (see FIGS. 1C and 2A) extends coaxially along the guide wire 28 in order to maintain the expandable filter assembly 22 in its unexpanded, delivery position until it is ready to be deployed within the patient's vasculature. The expandable filter assembly 22 can be deployed by the physician by simply retracting the restraining sheath 30 proximally to expose the expandable filter assembly. Once the restraining sheath is retracted, the self-expanding frame 24 becomes uncovered and immediately begins to expand within the body vessel (see FIG. 2B), causing the filter element 26 to move into a deployed position as well.

An optional obturator 32 is affixed to the guide wire 28 distal to the filter assembly 22 to prevent possible "snowplowing" of the embolic filtering device as it is being delivered through the vasculature. The obturator can be made from a soft polymeric material, such as Pebax 40D, and preferably has a smooth surface to help the embolic filtering device travel through the body vessels and cross lesions while preventing the distal end of the restraining sheath 30 from "digging" or "snowplowing" into the wall of the body vessel. The end of the delivery sheath 30 partially extends over the obturator 32 (FIG. 2A) so that a smooth outer surface is created between these components.

In FIGS. 2A and 2B, the embolic filtering device 20 is shown as it is being delivered within an artery 34 or other body vessel of the patient. Referring specifically now to FIG. 2B, the embolic filtering assembly 22 is shown in its expanded position within the patient's artery 34. This portion of the artery 34 has an area of treatment 36 (FIG. 2A) in which atherosclerotic plaque 38 has built up against the inside wall 40 of the artery 34. The filter assembly 22 can be placed distal to and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in a variety of arteries or other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The expandable frame 24 includes a pair of half frames 42 and 44 (also referred to as D-frames) which, upon release from the restraining sheath 30, expand the filter element 26 into its deployed position within the artery (FIG. 2B). Embolic debris created during the interventional procedure and released into the body fluid is captured within the deployed filter element 26. Although not shown, a balloon angioplasty catheter could be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) can be implanted in the area of treatment 36 using over-the-wire or rapid exchange techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris 41 created during the interventional procedure will be released into the bloodstream and will enter the filter element 26. Once the procedure is completed, the interventional device may be removed from the guide wire. The filter assembly 22 thereafter can be collapsed and removed from the artery 34, taking with it any embolic debris trapped within the filter element 26. A recovery sheath (FIG. 8) can be delivered over the guide wire 28 to collapse the filter assembly 22 for removal from the patient's vasculature.

Referring specifically now to FIGS. 1A-1H, the particular embodiment of the frame 24 includes a first half frame 42 and second half frame 44 which cooperatively form a deployment mechanism for expanding the filter element 26 within the patient's vasculature. As can be seen in these figures, the first half frame 42 includes a first control arm 46 and a second control arm 48 connected to each other via a partial loop 50 which extends radially outward once placed in the deployed position as is shown in FIG. 1B. Likewise, the second half frame 44 includes a first control arm 52 and a second control arm 54 connected by a partial loop 56. These partial loops form a D-shaped structure when placed in an expanded position. Once placed in the deployed position, as is shown in FIG. 1B, the partial loops 50 and 56 cooperatively form a composite circular shaped loop having a large opening to which the filter element 26 is attached. In this fashion, once the first half frame 42 and the second half frame 44 are deployed, the partial loops 50 and 56 will self-expand radially to contact the wall of the artery to maintain proper wall apposition to prevent gaps from forming between the filter element 26 and the wall of the body vessel. These half frames are sometimes referred to as D-frames since the partial loops form a D-shape once deployed. (See FIG. 1H.) The two half frames may be connected together by a wire, glue or solder at, or substantially near, the X marks shown in FIG. 1B. This connection helps to prevent the half frames from twisting relative to each other. Such a connection can be utilized with any of the other embodiments of the present invention. Any embolic debris or unwanted particles which may be entrained in the body fluid passing through the body vessel should be captured in the filter element.

The filtering assembly 22 is rotatably mounted onto the guide wire 28 via a filter support structure 58. This filter support structure 58, shown in the embodiment of FIGS. 1A-1B, 1D-1H as a filter coil 60, provides a suitable amount of flexibility and bendability to the composite filter assembly as the device is being delivered through the sometimes tortuous paths leading to the area of treatment. As can be seen in FIGS. 1A and 1B, this filter coil 60 can extend from a position proximal to the frame 24 to a position distal to the end of the filter element 26. While a wire coil is utilized to form this filter coil 60, it should be appreciated by those skilled in the art that other components could be utilized to create this filter support structure 58 without departing from the spirit and scope of the present invention. For example, a piece of tubing made from a polymeric material or a nickel-titanium hypotube having good flexibility also could be utilized as the filter support structure. A suitable material for the filter coil includes 304 stainless steel spring wire having a diameter of about 0.002±0.0002 inches.

As can best be seen in FIGS. 1A-1C, each of the first and second control arms of the first half frame 42 and the second half frame 44 are connected at a sleeve or collar 62 located proximal to the partial loops 50 and 56. In this regard, the ends of each of the first and second control arms are connected substantially together by this collar 62. This collar 62 can be mounted over the ends of the first and second half frames to maintain the ends fixedly disposed between the collar 62 and the filter coil 60. This collar 62 can be made from a highly radiopaque material such as a platinum/iridium alloy having a material composition of 90% platinum and 10% iridium. More specifically, FIGS. 1D and 1E show one particular arrangement for mounting the half frames to the filter coil 20. Solder 66 is placed over the ends of the first and second half frames in order to create a smooth, tapered surface with the outer surface of the collar 62. A tapered solder joint 66 located proximal to the collar 62 also can be utilized to help maintain the first and second half frames mounted onto the filter coil 60. This solder joint 66 also provides a smooth taper with the outer surface of the collar 62. It will be appreciated by those skilled in the art that still other ways of mounting the first and second half frames onto the filter support structure 58 can be implemented in accordance with the present invention.

As can best be seen in FIGS. 1A-1C, the filter assembly 22 is disposed between a proximal stop fitting 68 and distal stop fitting 70 placed on the guide wire 28. In this manner, the stop fittings 68 and 70 abut against the ends of the filter coil 60 to either inhibit longitudinal motion of the filter assembly 22 relative to the guide wire completely or to provide a limited range of motion along the guide wire. As is shown in the same figures, the proximal fitting 68 and distal fitting 70 are placed in close proximity to the ends of the filter coil 60 to prevent any appreciable amount of longitudinal motion of the filter assembly 22 relative to the guide wire 28. However, the spacing between the proximal fitting 68 and distal fitting 70 could be increased to allow a limited range of motion of the filter assembly relative to the guide wire. Additionally, this particular mounting system allows the filter assembly 22 to be rotatably mounted onto the guide wire 28 to permit the guide wire 28 to rotate freely once the first and second half frames 42 and 44 are deployed in the body vessel. In this manner, if the physician should spin the guide wire at its proximal end while placing an interventional device on the guide wire, that rotation will not be transmitted along the guide wire to the deployed wire frame 24. Thus, the frame 24 and the filter element 26 should remain stationary in the event of accidental or intentional rotation of the guide wire at its proximal end.

Referring now to FIG. 2A, the first half frame 42 and second half frame 44 are shown in a collapsed, delivery position within the restraining sheath 30. As can be seen in FIG. 2A, the first and second control arms and partial loop forming the half frames actually define a single, complete loop which extends in a longitudinal fashion within the restraining sheath 30. In order to release the crossing profile of the restraining sheath 30, the control arms should be brought together as close as possible when collapsed. Once the restraining sheath 30 has been retracted, the self-expanding properties of the material used to manufacture the first and second half frames 42 and 44 allow the partial loops to radially expand outward to the deployed position shown in FIG. 2B. The control arms will expand radially outward to some degree as well. Once deployed, the partial loops 50 and 56 cooperatively form a complete circular loop which forms an opening for the filter element 26.

In order to maintain a small crossing profile, the delivery sheath 30 should have a small diameter to create the small crossing profile, yet must be large enough to house the collapsed filtering assembly 22 therein. As can be seen in FIG. 2A, each of the half frames must be sufficiently collapsed in order to fit within the lumen of the delivery sheath 30. In order to assist in reaching this collapsed position, it may be beneficial to place a region of articulation 72 on each of the partial loops 50 and 56 of the first and second half frames. This articulation region 72 can be formed, as is best shown in FIGS. 1B and 1F, as a D-shaped bend region located at the apex or near the apex of each of the partial loops. This articulation region 72 helps to collapse the half frame into the sheath 30. The addition of this articulation region 72 at the apex of the partial loop also increases the surface area for improved distribution of the expansional force exerted by the device to the interior wall of a body vessel once deployed. It also improves the radiopaque image created by the device during fluoroscopy.

As can be seen in FIGS. 1B and 1G, this articulation region 72 extends from the substantial D-shape of the expanded loop portion and is substantially parallel with a linear axis defined by the guide wire. In this respect, as can be seen in FIG. 1G, the articulation region extends distally away from the partial loop and is almost perpendicular to the linear axis defined by the expanded partial loop. The particular embodiments shown in FIGS. 1A-1F, this articulation region 72 is shown as having a D-shape and is placed near or at the apex of the expanded partial loops. The D-shape of the articulation region 72 enables the half frame to more easily collapse to its delivery position within the delivery sheath since the partial loop now is preformed with a working "hinge" that allows the control arms to more easily collapse closer to each other.

The D-shaped partial loops 50 and 56 shown in this embodiment also include a radiopaque wire coil 74 which can be wrapped around each partial loop to enhance the radiopacity of the device under fluoroscopy. Since nickel-titanium or a specially processed nickel-titanium can be utilized to create the frame 24 of the present invention, there may be a need to increase the radiopacity of the device under fluoroscopy since nickel-titanium and nickel-titanium-based alloys generally have low visibility during fluoroscopy. In this regard, a very small diameter wire 74 can be wrapped around the partial loops forming the half frames to increase visualization of the device during fluoroscopy. One suitable material for this radiopaque wire includes gold plated tungsten wire having about 5-7% gold plating. The wire can have a diameter of about 0.0010±0.0002 inches, although the diameter can vary depending on the size of the expandable frame 24. It should also be appreciated that other radiopaque markers and marking systems could be utilized in conjunction with the filter assembly 22 in order to enhance visibility during fluoroscopy.

Referring now to FIG. 1I, a particular embodiment of an expandable frame 24 is shown with the lengths of the first and second control arms of the first and second half frames 42 and 44 varied to achieve an offset or gap between the two half frames. As can best be seen particularly in FIG. 1I, the first and second control arms 46 and 48 of the first half frame 42 have a length which is longer than the length of the first and second control arms 52 and 54 of the second half frame 44. The length of the control arms is generally measured from the end of the arm as mounted to the collar 62 up to the transition area where the partial loop starts to extend radially away from the arm in the deployed position. In this manner, the first half frame 42 has control arms of unequal length to the second half frame 44 which may be useful when deploying the filtering assembly 22 in curved portions of the anatomy. As a result, when the frame 24 is expanded into its deployed expanded position, the differences in the lengths of the control arms create a gap between the positioning of the partial loops 50 and 56. This gap is indicated by arrows in FIG. 1I. Additionally, this offset or gap between the first and second half frames helps when retracting the filter assembly back into a recovery sheath or into the delivery sheath since the length of the first and second half frames will be different in the collapsed delivery position as well. As a result, one of the half frames will take a position that is not in direct contact with a portion of other the half frame which may make it easier to retrieve the frame into either the delivery or recovery sheath.

It should be noted that in the embodiment of FIG. 1I, the frames include partial loops which do not include the D-shaped articulation region 72, as is shown in the previously described embodiment. It should be noted that an articulation region is not always required in order to properly deploy and collapse the half frames.

Referring now to FIGS. 1J and 1K, an alternative embodiment for the mounting of the expandable frame 24 of the embolic filtering assembly 22 to the guide wire 28 is shown. In this particular embodiment, the frame 24 includes the same or similar first half frame 42 and second half frame 44 as shown in FIGS. 1A-1H. This particular embodiment differs from the previous embodiment in the manner in which the filtering assembly 22 is mounted onto the guide wire 28. As is shown in FIG. 1J and 1K, the filtering assembly 22 is not mounted onto a filter support structure 56, such as the filter coil 60, but rather, the ends of each of the first and second half frames 42 and 44 are mounted to a collar 62 which is in turn rotatably mounted onto the guide wire 28. A proximal fitting 68 is placed on a guide wire along with a distal fitting 70 to maintain the collar 62 in a free spinning orientation on the guide wire. The proximal and distal fittings can be placed in close proximity to the collar to prevent longitudinal motion relative to the guide wire or spaced further apart to permit some longitudinal motion. A different shaped obturator 32 can be used with this modified embodiment and is located at the distal end of the filter element 26. This particular obturator is slidably fixed to the guide wire 28 to allow the distal end of the filter assembly 22 to move along the guide wire between collapsed and expanded positions. Like the previously described embodiment, the half frames may include an articulation region 72 and radiopaque wire 74 wrapped around the partial loops. The deployment and recovery of this particular embodiment of the embolic filtering device is similar to that shown in FIGS. 1A-1H and described above.

Referring again to FIG. 1G, the partial loops 50 and 56 are shown disposed at an offset angle θ which in this particular embodiment is an angle of about 100 degrees. It should be appreciated that the angle θ is measured from the linear axis defined by the guide wire and the linear axis defined by the position of the deployed partial loop. This angle θ can be increased or even decreased as needed. In this regard, the partial loops can be deployed at a substantial perpendicular angle, or 90 degrees. This angle θ also can be increased beyond 100 degrees which will create a smaller overall diameter once deployed in the patient's vasculature. It should be appreciated that when the filtering device is placed in a body vessel that is smaller in diameter than the fully expanded diameter formed by the partial loops 50 and 56, the elastic nature of the wire forming the half frames may naturally increase the angle θ in order to conform to the smaller diameter of the artery. This shows the advantage of the half frame structure since a larger diameter frame can be placed in a smaller diameter vessel. In this regard, while a preferred angle θ may be about 100 degrees, if the filter device is deployed in a smaller artery, angle θ will increase as needed in order to conform the filter device within the body vessel.

Referring now to FIGS. 3A-3F, another embodiment of an embolic filtering device 80 is shown. This particular embodiment is somewhat similar to the embodiment shown in FIGS. 1J and 1K. Referring specifically to FIGS. 3A and 3B, the embolic filtering device 80 includes a filter assembly 82 having an expandable frame 84. A filter element 86 is attached to the filter expandable frame 84 and moves with the expandable frame 84 between a collapsed delivery position and a deployed position. The expandable frame 84 includes a first half frame 88 and a second half frame 90 which cooperate to form a deployment mechanism for expanding the filter element 86 within the patient's vasculature. The first half frame 88 includes a first control arm 92 and a second control 94 connected together by a partial loop 96. Likewise, the second half frame includes a first control arm 98 and second control arm 100 connected by a partial loop 102. These partial loops 96 and 102 formed on the first and second half frames 88 and 90 likewise create a D-shaped structure once placed in the expanded position (FIG. 3E). In this deployed position, the first and second half frames cooperate to create an opening which maintains the filter element 86 in a deployed position against the wall of the body vessel. Each of the partial loops 96 and 102 includes an articulation region 104 which like the previously described embodiment, can be D-shaped in order to help in the collapse of the half frames for delivery within the delivery sheath.

Referring specifically now to FIG. 3E, each of the partial loops 96 and 102 have an articulation region 104 formed at or near the apex of the partial loop. There are three different radii formed on the partial loops 96 and 102 which create strain distributing bends shaped in such a way that most of the bending of the wire which forms the half frame is shifted from one point at the apex of the partial loop to the three different radii that define the strain distributing bends. The first strain distributing bend is the arbitration region 104 formed at or near the apex of the D-shaped partial loop. The other strain distributing bends 106 and 108 are located directly to the left and right of the articulation region 104. Each of these strain distributing bends 106 and 108 have a particular radii which helps to distribute the strain when the partial loop moves between the collapsed position and expanded position. Each of these strain distributing bends 106 and 108 generally have a radius substantially equal to each other, although it is possible to use different sizes of radii. The radius of the D-shaped articulation region 104 is usually larger than the other two strain distributing bends and is offset from a "normal" shape of the "D" (indicated by dotted lines in FIG. 3E). This offset or gap of the radius of the articulation region 104 with the "normal" D-shape is indicated by arrows in FIG. 3E. This offset or gap can have a length from approximately one diameter up to about 20 diameters of the wire used to form the partial loop. In this way, the further the radius is set from the "normal" D-shape, the more it will bend before the strain distributing bends 106 and 108 actually start to bend. The optimum strain condition is reached when the strain distributing bends 106, 108 and the articulation region 104 are substantially equal.

Referring now to FIGS. 3D and 3F, the particular angulation of the half frames 88 and 90 are shown in greater particularity. Referring now specifically to FIG. 3F, the partial loops 96 and 102 are shown as when placed in a normal expanded position. In this regard, the angle ÿ again defines the angle formed between the linear axis of the guide wire and the linear axis extending through the expanded partial loop. Again, as with the previously described embodiment, this angle ÿ can be from about 90 degrees, such that the partial loops are substantially perpendicular with the linear axis defined by the guide wire, or it can be greater than 90 degrees depending upon, of course, the final diameter which is desired to be created by the two partial loops 96 and 102. As shown in FIG. 3F, the angle ÿ is approximately 100 degrees.

The articulation regions 104 formed on each half frame are shown substantially in the same linear axis as the expanded partial loops. However, the angulation of the articulation region 104 can be varied as is shown by the angle ÿ in FIG. 3F. Here, the articulation regions 104 can be directed at an angle ÿ from about zero and 90 degrees, as may be required for a particular application. This angle ÿ can be as large as 90 degrees to create the articulation region as is shown in FIG. 1G. The angle ÿ can be varied to obtain the exact strain relief or strain distributing bends which will be necessary for a particular material or particular diameter of wire that may be used in forming the half frames.

Referring now to FIG. 3C, a cross-sectional view of one type of wire which can be utilized in creating the expandable frame is shown. In FIG. 3C, the composite wire 110 is made from a number of wire strands 112 which cooperate to form a single wire. These multiple strands 112 forming the composite wire can be encapsulated by a polymeric material 114, such as polyurethane, to help prevent the strands 112 from unraveling during assembly or usage. Alternatively, the expandable frame could be formed by a single wire, rather than multiple wire strands. It should be appreciated that any of the embodiments of the invention described herein could be made from either a single solid wire or multiple wire strands without departing from the spirit and scope of the present invention. When a multiple strand wire is utilized to create the frame, it is possible that some of the wire strands could be made from different materials other than, for example, nickel-titanium. In this regard, some of the strands could be made from a material having higher radiopacity than nickel-titanium to enhance the visualization of the expandable frame during fluoroscopy. In the particular embodiment shown in FIGS. 3A-3E, radiopaque coils (not shown) could be wrapped around the partial loops of the half frames to increase visualization during fluoroscopy. Also, it should be appreciated that although this particular embodiment of the filtering device is shown as being mounted between proximal and distal fittings placed on a guide wire 28, it is possible to utilize the filter support structure (filter coil) to mount the expandable frame onto the guide wire, as is shown in the embodiment of FIGS. 1A-1H. The same mounting structure could be used for any of the embodiments described and disclosed herein.

Referring now to FIGS. 4A-4C, an alternative embodiment of an embolic filtering device 120 is shown. This particular variation includes a filter assembly 122 having an expandable frame 124 to which is attached a filtering element 126. The expandable frame 124 is different from the other disclosed embodiments of the expandable frame in that a single frame is utilized, rather than two separate half frames which cooperatively form the expandable frame. In this regard, the expandable frame 124 includes a pair of control arms 128 and 130 which extend from a proximally mounted location to a divergence where a pair of partial loops 132 and 134 is connected. The partial loops 132 and 134 function in substantially the same manner as the previously described loops in order to expand together to form a substantially circular diameter used as a deployment means for maintaining the filter element 126 deployed within the body vessel. The ends 133 and 135 of these control arms 128 and 130 translate to a substantially Y-shaped transition region where the partial loops 132 and 134 of the frame are connected. In this particular embodiment, the expandable frame 124 eliminates a set of control arms by creating a single set of arms which can be expanded while holding the filtering element 126 in place utilizing a pair of partial loops 132 and 134. This particular embodiment utilizes a collar 136 to which the proximal ends 138 and 140 of the control arms are attached. This particular collar 136 can be rotatably mounted on the guide wire 28 to permit rotation between components. Additionally, the proximal fitting 68 and distal fitting 70 can be placed on the guide wire to limit or eliminate relative longitudinal motion between the filtering assembly 122 and the guide wire 28. Although not shown in FIGS. 4A-4C, this particular expandable filter 124 can include partial loops 132 and 134 including articulation regions and strain distributing bends as those described and disclosed in the previous embodiments of the filter device. Also, this particular embodiment also could be mounted onto a filter support structure, such as a filter coil 60, as previously discussed.

Referring now to FIG. 5A-5D, a variation of the previously described filtering device 120 is shown. In this particular embodiment, the expandable frame 124 has essentially the same shape as shown in FIGS. 4A and 4B except that there are strain distributing struts 150 formed at bend points on the frame to help distribute to strain at certain locations where maximum strain can be developed to at least minimize the strain in the expandable frame. Referring specifically to FIGS. 5A and 5B, these strategically placed strain distributing struts 150 are located at bend points which exist at a Y-shaped transition portion where the control arms 128 and 130 terminate and extend into the partial loops 132 and 134 of the frame. In this manner, the strain distributing strut 150 is simply a reduced width of the strut which forms the frame. As a result, it will be easier to collapse the partial loops into the delivery sheath and to retrieve the device after it has been deployed in the patient. Additionally, the apex of the partial loops is another location where a strain distributing strut of reduced strut thickness can be placed to help reduce the strain developed on the partial loop. Additional strain distributing struts could be placed where needed in order to help facilitate bending. The strain distributing strut could also be formed by reducing the thickness of the strut forming the frame or a combination of reduced width and thickness.

Referring now specifically to FIGS. 5C and 5D, the cross-section of the struts which form the expandable frame is shown in greater detail. As can be seen from these figures, the cross-sectional profile of the strut at these locations are generally rounded squares which somewhat simulate the bending characteristics of a round wire. It should be appreciated that the expandable frames shown in FIGS. 4A-4C and 5A and 5B can be formed by cutting a tubular segments such as a nickel-titanium tubing, with a laser. In this manufacturing process (which will be described in further detail below), the laser will selectively remove portions of the tubing to create the strut pattern which forms the expandable frame. Generally speaking, when tubing is cut by the laser, the laser cuts at a 90 degree angle with the surface of the tubing. Therefore, a substantially square or even rectangular cross-sectional shape will be created when utilizing such a laser manufacturing procedure. However, the laser cut frame can be further processed by chemically etching the struts to round off the sharp edges or rectangular cut. In this regard, the rounded square or rectangular cross-sectional strut will more closely simulate a round wire which generally has better bending properties than a square or rectangular cross-sectional strut. The frame can be chemically etched using known techniques in the art.

Referring now to FIG. 6A-6C, yet another embodiment of a filtering device 200 is shown. This particular embodiment of an embolic filtering device 200 includes a filter assembly 202 having an expandable frame 204 which is best seen in FIG. 6B. A filter element 206 is attached to the expandable frame 204 in order to collect unwanted particles which may be entrained in the body fluid of a body vessel. The filter assembly 202 is mounted to a guide wire 28 in much the same manner as with the previously described embodiments. This particular expandable frame 204 is somewhat similar to the embodiment of FIGS. 5A-5C, in that the expandable frame includes a pair of flexible control arms 208 and 210 from which extends a pair of partial loops 212 and 214. This expandable frame 204, however, includes an additional set of distal control arms 216 and 218 which extend distally from the connection point where the proximal control arms 208 and 210 are connected to the partial loops 212 and 214. This pair of distal control arms 216 and 218 extend distally to a collar (not shown) which is rotatably mounted onto the guide wire. Likewise, the ends of the proximal control arms 208 and 210 are attached to a rotatable collar 220 which allows the expandable frame 204 to spin relative with the guide wire. A proximal stop fitting 222 and distal stop fitting 224 placed about the proximal collar 220 helps to prevent or limit the amount of longitudinal movement of the filter assembly 202 relative to the guide wire and also prevents the distal and proximal ends of the filter from rotating independently and getting tangled so it will not open.

Referring now specifically to FIG. 6C, the "Y" shaped connection of the expandable frame 204 is shown in greater detail. As can be seen in this particular figure, the ends of the partial loops have a strain distributing struts 226, again shown as a thin strut widths, that enhance bendability at bend points in the frame. The distal control arm 216 which extends from the "Y" junction can have the same strut width with the proximal control arm 208, as is shown in FIG. 6C, or it may include a thinner strut to allow the distal control arms to bend more freely. Likewise, the proximal control arms also could have a smaller strut width proximal to the "Y" transition to allow the frame to bend more easily and to help reduce and distribute the strain developed when the frame moves between collapsed and expanded positions.

Referring now to FIG. 7, a special torque handle device 230 which can be utilized in conjunction with the delivery sheath of FIG. 1C is shown. This torque handle 230 can be mounted directly to the guide wire 28 and is utilized by the physician in steering the embolic filtering system, for example, within the patient's vasculature. The torque handle 230 is modified to include a side port 232 having a lumen which receives the delivery sheath 30. As can be seen in FIG. 1C, the delivery sheath 30 includes a distal tip section 234 adapted to receive the filtering assembly in its collapsed state. The delivery sheath also includes a shaft portion 235 including a split seam channel or slit 236 which extends from the distal tip section to a proximal end of the delivery sheath. The proximal portion of the delivery sheath includes a proximal grip portion 238 to aid in the handling of the sheath. This thin wall channel or slit 236 allows the delivery sheath to be peeled away from the guide wire after the embolic filtering device has been properly positioned in the patient. The side port 232 provides a handy means for facilitating the peel away feature of the delivery sheath since the physician or assistant needs to only hold onto the torque handle and retract the delivery sheath through the side port. As the delivery sheath is retracted distally, the split seam channel or slit separates which enhances the speed and ability in withdrawing the deliver sheath from the patient. It should be appreciated that the split seam also can be a line of reduced wall thickness found in the sheath. The thinner wall forms a weakened area in the wall of the sheath which can be easily split by the retraction of the sheath within the side port of the torque handle.

Figure 8:
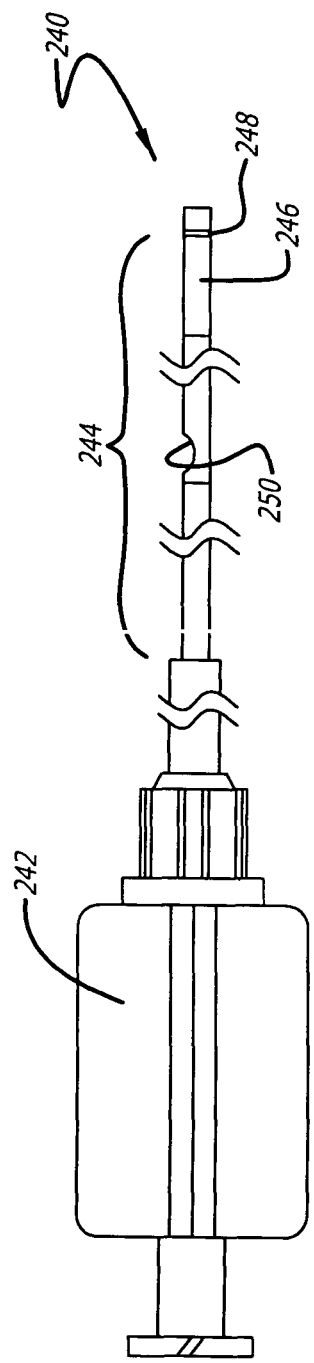
FIG. 8 is a side elevational view of a recovery sheath which utilizes rapid exchange technology that can be used to recover the embolic filtering device after it has been implanted in patient.

Referring to FIG. 8, a recovery sheath 240 which can be utilized with any of the embodiments of the embolic filtering device is shown. This recovery sheath 240 provides a means to retrieve the filter assembly after the filter has been utilized to retrieve particles from the body vessel. The recovery sheath 240 includes a side arm adapter 242 which is located at the proximal end of the sheath. The shaft 244 of the recovery sheath extends approximately 140 centimeters to a distal end section 246. A radiopaque marker 248 may be placed near the distal end section 246 of the shaft to aid in visualization during fluoroscopy. The shaft 244 includes a guide wire notch 250 located proximal to the distal end section 246 is used to receive the guide wire. In this respect, the recovery sheath may utilize rapid exchange (RX) features for quickly and easily placing the recovery sheath into the target location for retrieval of the filtering assembly. The distal end section 246 may be somewhat flared outward to a larger diameter than the diameter in the proximal portion of the shaft in order to provide a large lumen for retrieval of the expanded filter. It should be appreciated by those skilled in the art that other types of recovery sheaths could be utilized as well in retrieving the embolic filtering device from the patient.

Figure 10A:
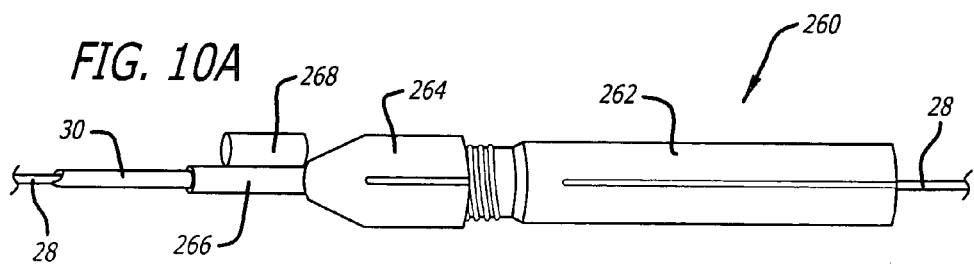
FIG. 10A is a side elevational view of a torque device having a side port which can be used to peel away the delivery sheath, similar to the one shown in FIG. 7.
Figure 10B:
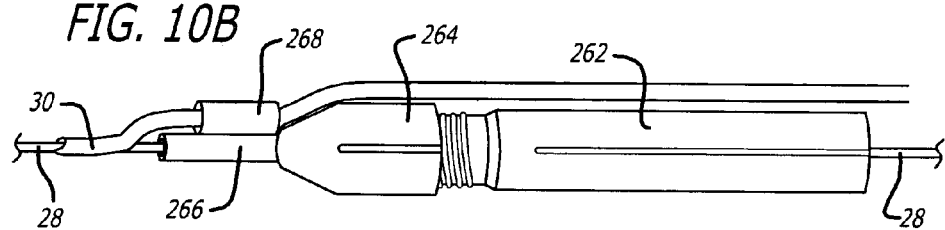
FIG. 10B is a side elevational view of the torque device of FIG. 10A showing the delivery sheath being peeled away from the guide wire.

Referring now to FIGS. 10A and 10B, another embodiment of a special torque device 260 which can be utilized in conjunction with the delivery sheath 30 of FIG. 1C is shown. This torque device 260 can be attached to a guide wire 280 and utilized by the physician to steer the embolic filtering system and guide wire within the patient's vasculature. The torque device 260 includes a handle 262 and a cap 264 which is utilized to squeeze the guide wire 280 via a collet within a lumen (not shown) that extends through the torque handle 260. The cap 264 includes a cap extension 266 utilized to receive the guide wire 28, along with a side port 268 attached directly to the cap extension 266, as is shown in FIGS. 10A and 10B. This side port 268 functions much like the side port 232 of the torque device of FIG. 7. In this regard, the end of the delivery sheath 30 is adapted to extend through this side port 268 when the delivery sheath 30 is to be removed from the patient's vasculature. Once the end of the delivery sheath is placed in the side port 268, the physician merely retracts the sheath to cause a splitting or "peeling" action that causes the sheath to split. The delivery sheath 30 may include a split seam channel or slit (not shown) which extends from the distal end of the delivery sheath to the proximal end. This split seam channel or slit allows the delivery sheath to be more easily peeled away from the guide wire after the embolic filtering device has been properly positioned in the patient. In this fashion, the side port 268 provides a means for facilitating the peeling away feature of the delivery sheath since the physician or assistant only needs to hold one end of the torque handle and retract the delivery sheath through this side port 268. In the embodiment shown in FIGS. 10A and 10B, this side port 268 is placed on the torque device close to the axis of the guide wire in order to maintain an angle which allows the sheath 30 to be easily split and removed from its coaxial relationship with the guide wire 28.

Figure 11A:
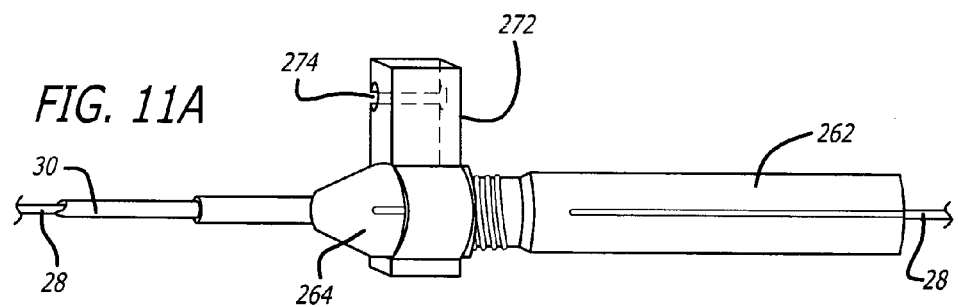
FIG. 11A is a side elevational view of a sheath clip which can be attached to a torque device to create a side port which can be used to peel away the delivery sheath.
Figure 11B:
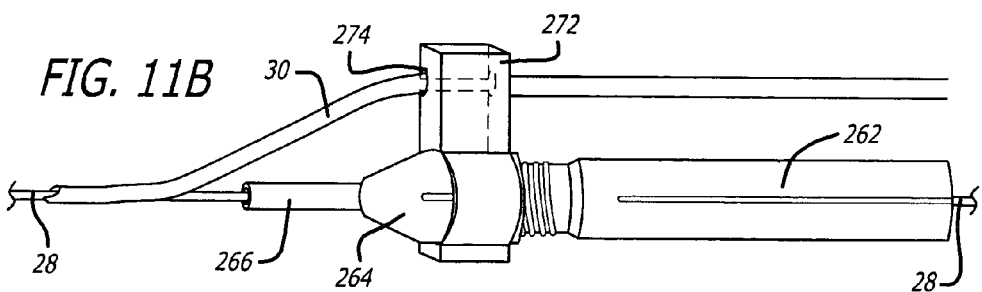
FIG. 11B is a side elevational view of the sheath clip and torque device of FIG. 11A showing the delivery sheath being peeled away from the guide wire.

Referring now to FIGS. 11A and 11B, another embodiment of a special torque device 270 is shown. This particular embodiment, the torque device 270 includes the handle portion 262 and cap 264, as is shown in the previous embodiment of the torque device. A peel-away clip 272 is attached to the cap 264 of the torque device to create a removable side port 274. As can be seen in FIGS. 11A and 11B, this peel-away clip 272 can be placed, for example, on the cap 264 of the torque device 270 to modify a conventional torque device into a special torque device which can be utilized to facilitate the peel-away feature of the delivery sheath. This particular device provides much the same features as the torque handle device 230 shown in FIG. 7. This side port 274 could be manufactured as a continuous lumen which extends through the peel-away clip 274 or a split channel as is shown in this particular embodiment. This split channel helps to facilitate the placement and removal of the sheath 30 into the side port 274. It should be appreciated that this particular peel-away clip 272 could be directly molded into the cap portion of the torque device, or could be a clip-on device which could be attached to a commercially available torque device. It also should be appreciated that the peel-away clip 272 could be mounted to other components of the torque device, such as the handle 262, without departing from the spirit and scope of the present invention.

Referring now to FIGS. 12A-12C, another embodiment of a special torque device 280 is shown. As with the previous embodiment, this particular device can be either a clip-on device which can be attached to a conventional torque device 260 or can be molded with the end cap 264 to create an integral unit. As can be seen in FIGS. 12A-12C, the torque device 280 includes a torque handle 262 having a lumen (not shown through which the guide wire 28 extends. The torque handle 262 is directly mounted to the guide wire 28 and can be locked onto the guide wire via the cap 264. This handle 262 allows the physician to manipulate and rotate the guide wire 28. The torque device 280 includes an extension arm 284 having a first end 282 which is attached to, for example, the cap 264. This extension arm 284 extends from the first end 282 and translates to a second end 286 which includes an opening 285 (shown in dotted lines) that receives both the delivery sheath 30 and guide wire 28. This opening 285 can be made with a funnel shape with the wide mouth opening on the distal end of the arm 284 to allow for easy entry of the proximal end of the guide wire 28 and sheath 28. A similar opening 287 extends into the body of the torque device. This opening 287 also can be funnel shaped to facilitate ease of entry of the proximal end of the guide wire 28 into the lumen of the handle 262. In this regard, the second end 286 helps to maintain the guide wire 28 and delivery sheath 30 centered along the same axis, as is shown in FIG. 12A. When the delivery sheath 30 is to be removed from the guidewire 28, the proximal end of the delivery sheath is placed through a side port 288 located near the first end 282 and pulled by the physician. This side port 288 also can have a funnel-shaped opening for ease of insertion of the proximal end of the sheath.

As is shown in FIG. 12B, the extension arm 284 and second end 286 help to maintain the sheath and guide wire along a same axis until the delivery sheath reaches the side port 288. This particular arrangement helps to prevent the guide wire 28 from "splaying" away from the delivery sheath 30 when the sheath 30 is being peeled from the guide wire 28. During "splaying" the proximal end of the sheath is removed from the guide wire while the very distal end of the delivery sheath 30 remains stationary. This condition gives the false sense that the filter device has been deployed, when the guide wire 28 has actually moved from a non-coaxial position, increasing the likelihood of kinking and damaging the guide wire 28 and embolic protection filter. This particular arrangement also helps to decrease the likelihood of kinking of the guide wire when the delivery sheath is being peeled away through the side port 288.

It should be appreciated to those skilled in the art that the length of the extension arm 284 can be varied to maintain the sheath 30 and guide wire along a central axis until the delivery sheath 30 is placed into the side port 288. The length of the extension arm 284 can help to prevent "splaying" of the wire and kinking of the wire during usage. Generally, when a 0.014 inch diameter guide wire is utilized, the distance between the opening 285 and opening 287 is in the order of about ½ inch to 1½ inch. Additionally, opening 285 should have a diameter in the order of about one to two times that of the outside diameter of the delivery sheath to help prevent the guide wire from kinking distal of the opening 285 as the sheath 30 is pulled proximately through openings 285 and side port 288. Additionally, as can be seen in FIGS. 12A-12B, this extension arm 284 has a curvature which allows the physician enough room for his/her fingers so that the torque device can be properly grasped by the physician in order to separate the sheath from the guide wire. However, the length of the extension arm 284 should not be too great, otherwise the guide wire might not have sufficient column strength to prevent wire buckling as the sheath is being pulled from the guide wire. It should be appreciated that it is important to ensure that the peeling of the sheath 30 is confined to the area between the openings 285 and opening 287. The peeling action can extend distal of the opening 285 if the opening 285 is not proportioned correctly to the sheath diameter or if the distance between the openings 285 and 287 is too great. If the peeling does extend distal to the opening 285, then the guide wire can be kinked as the sheath is pulled proximally through opening 285 and side port 288. Peeling action which occurs distally of opening 285 can cause wire kinking and/or failure in deployment of the device.

In the particular embodiment of the torque device 280 shown in FIG. 12D, an additional extension tubing 290 is shown extending from the second end of the torque device 280 in order to assist in maintaining the delivery sheath and guide wire along a central axis and also to help prevent "splaying" and "kinking" of the guide wire when the delivery sheath is being removed.

Although the various embodiments of the embolic filtering apparatus have been shown as being mounted between fittings attached to a guide wire, the embodiments shown can be also deployed in an over-the-wire fashion as well. The steerable guide wire can be first initially steered into the target location by the physician. Thereafter, the embolic filtering assembly, which includes the expandable frame and filter element, can then be delivered to the target area in an over-the-wire fashion via the guide wire. In this regard, the delivery sheath can extend over the embolic filtering assembly and be moved with the filter assembly over the guide wire to the distal end of the guide wire, where the filter assembly can then be deployed. Utilizing this technique, it may be easier to first steer the guide wire into the target area and thereafter deliver the filtering assembly into the target area using an over-the-wire technique. It should be appreciated that a fitting may be required on the guide wire to hold and maintain the filtering assembly to the wire once the filtering assembly has been delivered to the distal end section of the guide wire. Alternatively, the filter coil utilized in conjunction with the filter assembly could be connected with the distal coil wire of the guide wire as a means for holding the filter assembly in place. The filter coil could have a coil which is wound opposite the coil of the guide wire to allow some intermeshing of the components in order to maintain the filtering assembly stationary on the guide wire. Thereafter, once the interventional procedure has been performed, a recovery sheath could be utilized to recover the filter assembly, as has been described above.

The expandable frames of the present invention can be made in many ways. One way is to use a single wire made from a material possessing self-expanding properties. The wire can be set to the desired size and shape when placed in the expanded position. Another particular method of making the frame is to cut a tubular member, such as nickel-titanium hypotube, to remove portions of the tubing in the desired pattern for each half frame or full frame, leaving relatively untouched the portions of the tubing which are to form the control arms and partial loop(s). The tubing may be cut into the desired pattern by means of a machine-controlled laser. Prior to laser cutting the pattern, the tubular member could be formed with varying wall thicknesses which can be used to create flexing portions on the half frames.

The tubing or wire used to make the half frames could possibly be made of suitable biocompatible material such as nickel-titanium and spring steel. Elgiloy is another material which could possibly be used to manufacture the frames. Also, very elastic polymers could possibly be used to manufacture the frames.

The size is often very small, so the wire or tubing from which the half frames are made must necessarily have a small diameter. Typically, the tubing has an outer diameter on the order of about 0.020-0.040 inches in the unexpanded condition. The wall thickness of the tubing is usually about 0.076 mm (0.003-0.006 inches). The diameter of a wire that can be used to form the expandable frame can be as small as about 0.0002 inches, but preferably about 0.0036 inches. Of course, large diameter wire could be used as well. When multiple stranded wire is utilized, the diameter of the composite wire can be about 0.006 inches. As can be appreciated, the width and/or thickness at the strain distributing strut will be less. For frames deployed in body lumens, such as PTA applications, the dimensions of the tubing may be correspondingly larger.

While the present invention has been described as being made from wire having a circular transverse cross-sectional area, or from a multiplicity of strands making a composite stranded wire having circular cross-sectional diameter, it should be appreciated that the half frames of the present invention also can be made with wire having a non-circular transverse cross-sectional area (hereinafter a non-round wire). The use of non-round wire could be designed such that the frames would be able to collapse (when in the delivery or recovery sheath) to an even smaller profile than if the frame was constructed from standard round wire. In the collapsed position, the frames should have the smallest profile possible. When the filtering assembly is able to be collapsed to a small profile, the device may have improved distal access, improved lesion crossing capability, and better compatibility with smaller guiding catheters.

The non-round wire may be in a wire size (i.e., width, thickness, or diameter in a range of about 0.001 inch to 0.010 inch, but preferably in a range of about 0.002 inch to 0.006 inch). The transverse cross-sectional shape of the non-round wire which may be used, includes, but is not limited to, semi-circular (i.e., half round or D-shaped), square, rectangle and ovular. The non-round shape, or shapes, may be formed in the wire during the drawing process or by post-drawing processes that include, but are not limited to, rolling and stamping.

Generally, when the frame or half frame is to be laser cut, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished frame. The frame can be laser cut much like a stent is laser cut. Details on how the tubing can be cut by a laser are found in U.S. Pat. Nos. 5,759,192 (Saunders), U.S. Pat. No. 5,780,807 (Saunders) and U.S. Pat. No. 6,131,266 (Saunders) which have been assigned to Advanced Cardiovascular Systems, Inc.

The process of cutting a pattern for the frame into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the CO2 or Nd:YAG laser set-up. The program for control of the apparatus is dependent on the particular configuration used and the pattern to be ablated in the coding.

One suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of nickel-titanium can be utilized, as can other self-expanding alloys, to obtain the same features of a self-expanding frame made in accordance with the present invention.

In one example, the frame of the present invention can be laser cut from a tube of nickel-titanium (Nitinol) whose transformation temperature is below body temperature. After the pattern of each half frame is cut into the hypotube, the tubing is expanded and heat treated to be stable at the desired final diameter. Alternatively, the frames can be made from Nitinol wire with the shape of the frames being set via techniques well-known in the art. The heat treatment also can control the transformation temperature of the frame such that it is super elastic at body temperature. The transformation temperature can be set at or below body temperature so that the frame is superelastic at body temperature. The frame is usually implanted into the target vessel which is smaller than the diameter of the frame in the expanded position so that the control arms apply a force to the vessel wall to maintain the frame in its expanded position. It should be appreciated that the frame can be made from either superelastic, stress-induced martensite NiTi or shape-memory NiTi.

Another way of making the frame of the present device is to utilize a shape-memory material, such as nickel-titanium, which utilizes a machine-controlled laser. A tubular piece of material or wire could be utilized in this process. The frame could be manufactured to remain in its open position while at body temperature and would move to its unexpanded position upon application of a low temperature. One suitable method to allow the frame to assume a change phase which would facilitate the frame and filter element being mounted into the restraining sheath include chilling the filter assembly in a cooling chamber maintained at a temperature below the martensite finish temperature through the use of liquid nitrogen. Once the frame is placed in its collapsed state, the restraining sheath can be placed over the frame to prevent the frame from expanding once the temperature is brought up to body temperature. Thereafter, once the filtering device is to be utilized, the restraining sheath is simply retracted to allow the basket to move to its expanded position within the patient's vasculature. If super elastic NiTi is used, the frame/filter assembly can be simply back loaded into the restraining sheath. The frame would be "set" to the expanded position.

The frame also could be manufactured by laser cutting a large diameter tubing of nickel-titanium which would create the two half frames in its expanded position. Thereafter, the frame could be placed in its unexpanded position by back-loading the frame into a restraining sheath which will keep the device in the unexpanded position until it is ready for use. If the frame is formed in this manner, there would be no need to heat treat the tubing to achieve the final desired diameter. This process of forming the frame could be implemented when using superelastic nickel-titanium or shape-memory nickel-titanium.

In another manufacturing process for manufacturing the frame and/or half frames, the laser cut Nitinol tubing is preferably cold formed and specifically cold worked with no heat treatment such that it remains in a fully martensitic state. The cold working proceeds only at temperatures below the recrystallization temperature of the Nitinol alloy. Next, the laser-cut Nitinol tubing is cold worked to its desired expanded size. The desired expanded size is thus imparted or set into the laser cut tube.

Importantly, the laser-cut Nitinol tubing is not heat treated to prevent generation of any loading or unloading plateaus in the stress-strain curve. In an alternative embodiment, the Nitinol tubing may undergo heat treating for only very limited durations at low temperatures. The present invention recognizes that a significant difference between linear pseudoelasticity and non-linear pseudoelasticity is the absence or presence, respectively, of stress-induced martensite. It also recognizes that in order to set a particular shape in Nitinol, the Nitinol must be heat treated at a relatively high temperature for a short period of time. Under normal circumstances, this material would then exhibit non-linear pseudoelasticity and therefore would undergo a reversible phase transformation from austenite to martensite when strained above a particular minimum strain value to initiate this reversible transformation. When setting a shape under standard conditions, for example, 550 degrees C. for 5 minutes, the Nitinol exhibits essentially no springback; that is, its unconstrained shape after heat treatment is nearly identical to its constrained shape during heat treatment. The Nitinol does not spring back to its original shape prior to heat treatment. At the other extreme, linear pseudoelastic Nitinol with no heat treatment has 100 percent springback and always returns to its original, cold worked shape.

Springback is a continuous function between no heat treatment (100 percent springback) and ideal shape setting heat treatment (approximately zero percent springback). From an engineering perspective for design of Nitinol based pseudoelastic devices, less springback is sometimes more favorable than more springback. However, in some circumstances, linear pseudoelasticity may be preferable to non-linear pseudoelasticity. Therefore, the present invention, in addition to contemplating cold-worked only Nitinol, addresses that regime of heat treatment temperatures and times within which springback is adequately minimized to successfully impart a desired shape to the Nitinol structure and within which the Nitinol does not develop a stable and reversible martensitic phase.

In a preferred embodiment of the present invention, to achieve the linear pseudoelastic behavior, the binary nickel-titanium tubing has approximately 55.8 atomic percent nickel. The tubing must contain a minimum of approximately 38 percent cold working when measured by the reduction in cross-sectional area, and there is not to be any heat treatment following final cold reduction. As to the alternative embodiment, the present invention contemplates accumulated heat treatment of the tubing of up to 300 degrees C. for up to 5 minutes. Under ideal conditions, these process parameters should adequately ensure that the Nitinol remains martensitic without a phase change under stress.

Figure 9:
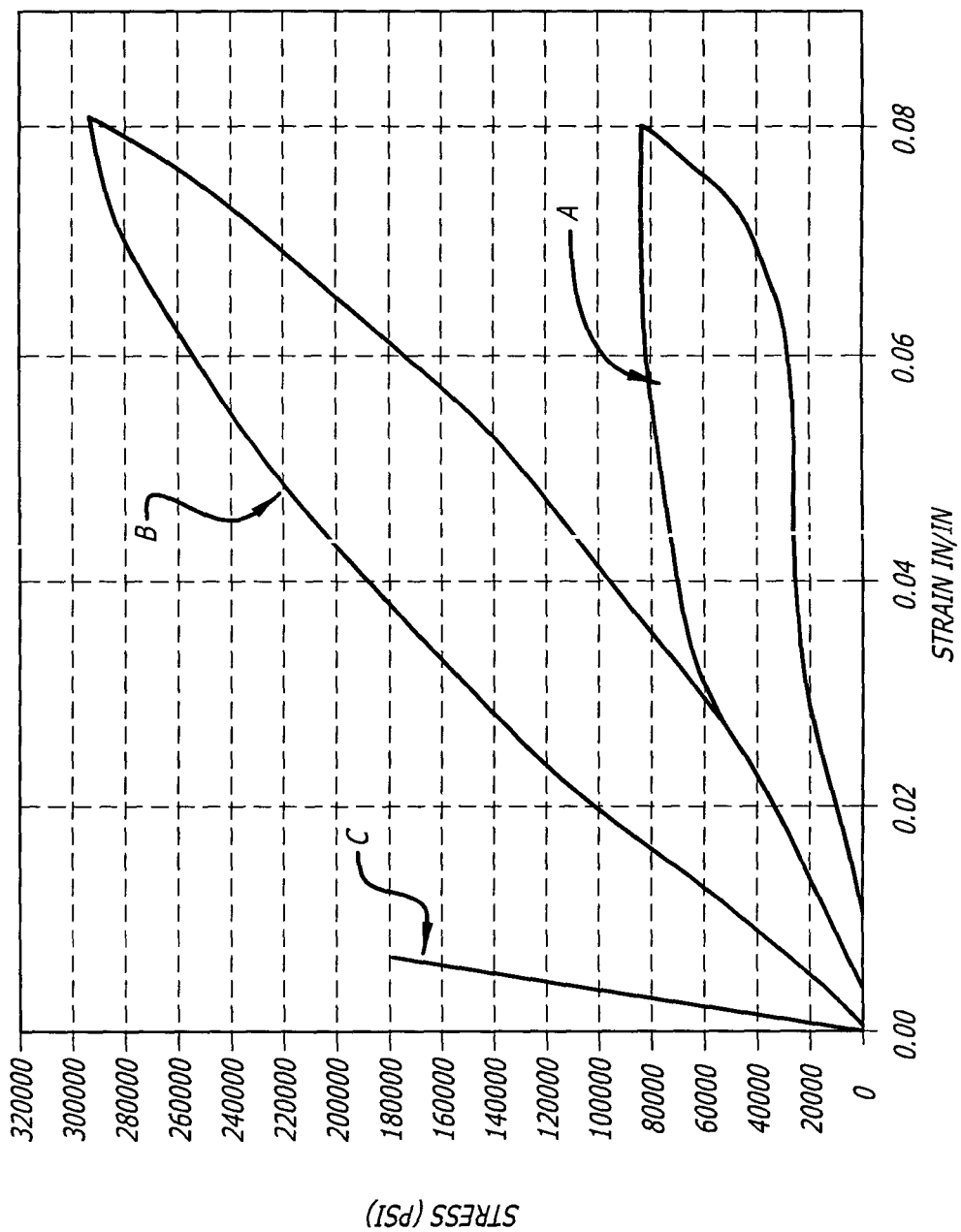
FIG. 9 is a set of stress-strain curves for conventional 316L stainless steel, linear pseudoelastic Nitinol, and non-linear pseudoelastic Nitinol.

To illustrate the foregoing points, FIG. 9 contains the elastic component of three idealized stress-strain curves for 316L stainless steel, linear pseudoelastic Nitinol, and non-linear pseudoelastic Nitinol. In a preferred embodiment, the expandable frame of the present invention is formed partially or completely of alloys such as the linear pseudoelastic Nitinol shown in FIG. 9.

In FIG. 9, in an idealized curve A for a non-linear pseudoelastic Nitinol, the relationship is plotted on x-y axes, with the x axis representing strain and the y axis representing stress. The x and y axes are labeled in units of stress from zero to 320 psi and strain from 0 to 9 percent, respectively.

In curve A, when stress is applied to a specimen of a metal such as Nitinol exhibiting non-linear pseudoelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve A this is represented by upper, nearly flat stress plateau at approximately 70 to 80 psi. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau at about 20 psi.

After the transformation back to austenite is complete, further stress reduction results in elastic strain reduction. This ability to incur significant strain at relatively constant stress upon the application of a load and to recover from the deformation upon the removal of the load is commonly referred to as non-linear pseudoelasticity (or superelasticity).

FIG. 9 also has a curve B representing the idealized behavior of linear pseudoelastic Nitinol as utilized in the present invention. Curve B generally has a higher slope or Young's Modulus than curve A for the non-linear pseudoelastic Nitinol. Also, curve B does not contain any flat plateau stresses found in curve A. This stands to reason since the Nitinol of curve B remains in the martensitic phase throughout and does not undergo any phase change. The same tension and release of stress cycle to generate curve A is used to generate curve B. To that end, curve B shows that increasing stress begets a proportional increase in reversible strain, and a release of stress begets a proportional decrease in strain. The areas bounded by curves A and B represent the hysteresis in the Nitinol.

As apparent from comparing curve B to curve A in FIG. 9, with the use of linear pseudoelastic Nitinol, the mechanical strength of the present invention medical device is substantially greater per unit strain than a comparable device made of superelastic Nitinol. Consequently, a major benefit is that smaller component parts such as struts can be used because of the greater storage of energy available in a linear pseudoelastic Nitinol device. A small profile is one critical factor for crossing narrow lesions or for accessing remote and tortuous arteries.

FIG. 9 includes curve C which is the elastic behavior of a standard 316L stainless steel. Stress is incrementally applied to the steel and, just prior to the metal deforming plastically, decrementally released. It is provided here simply for comparison to curves A and B.

As mentioned above, the present invention uses preferably a binary nickel-titanium alloy. In an alternative embodiment, however, the nickel-titanium may be alloyed with a ternary element such as palladium, platinum, chromium, iron, cobalt, vanadium, manganese, boron, copper, aluminum, tungsten, tantalum, or zirconium.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similar shape utilizing blow-mold or dip-mold technology. The openings can be any different shape or size. A laser, a heated rod or other process can be utilized to create perfusion openings in the filter material. The holes would, of course, be properly sized to catch the particular size of embolic debris of interest. Holes can be lazed in a spiral pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The material employed to manufacture the filtering element 26 can be modified thermoplastic polyurethane elastomer. Such elastomers can be prepared by reacting polyester or polyester diol, a short-chain diol, a diisocyanate, and a substituted diol. The isocyanate portion is commonly referred to as the hard segment and the diol as the soft segment. It has been found that such a material offers excellent flexibility along with resistance to broad temperature ranges or tough end-use environments. Moreover, the presence of substituted diol makes the urethane non-blocking (non-sticking) and thus desirable in many medical applications including filtering and embolic protection systems use.

The filter element can be made from thermoplastic polyurethane elastomers (TPU) made with substituted "diol." TPU's have both the mechanical as well as physical properties that are highly desirable in medical device applications. Filter element made with substituted "diol" TPU is non-blocking (non-sticking) and thus self adherence or undesirable adherence to other structures is minimized. Such a characteristic is a key to the effectiveness of a filter or other medical device as repeated manipulation and expansion and compression is common in the use of a filter. Thus, a filter made with modified TPU's (for example, modified Pellathane™), can consistently provide a surface or cavity for receiving matter and can be moved and expanded or contracted in vasculature to effectively accomplish its filtering function.

A combination of high tensile strength and high elongation of modified thermoplastic polyurethane elastomers contemplated makes the material well-suited for dip forming or molding applications. Notably, conventional methods such as blow molding inherently create stresses and tensions in the element being blow molded. Where the element is a filter element, such stresses can make it difficult to attach the filter element to a frame or other structure by a melting process. Since dip forming or molding is a manufacturing option, the filter element can be made very thin.

In a preferred method, a solution of desirable filter material is mixed or formulated. A mandrel having the general shape and size of the filter frame or other medical device is dipped into the solution, removed and allowed to dry. The dipping and drying steps are repeated as necessary to create an element with desirable characteristics. Once the dip molding is contemplated, the element created is further processed for preparing the element to be attached to a frame or medical device. The further processing involves removing any unwanted material or cutting openings in the element.

In certain applications, it may be desirable to apply a biocompatible lubricous coating to the filtering device. Such a lubricous coating can be Dow Corning 360 or other known biocompatible coatings. The coating can aid in the use of the filtering device for example, by facilitating deployment and manipulation. The filter element itself can be coated as well as the frame or cage to which it is attached.

The materials which can be utilized for the restraining sheath can be made from polymeric material such as cross-linked HDPE. This sheath can alternatively be made from a material such as polyolifin which has sufficient strength to hold the compressed filter assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed:

1. An embolic filtering system used to capture embolic debris in a body vessel, comprising:
   an expandable filter assembly including a self-expanding frame moveable between an expanded position and an unexpanded position, the expandable filter being disposed on a guide wire;
   a filtering element attached to and movable with the frame;
   a sheath having a lumen for receiving the guide wire and having a distal end portion and a proximal end, the distal end portion of the sheath being adapted to receive the expandable filter assembly for maintaining the filter assembly in the unexpanded position and being movable to expose the filter assembly; and
   a torque device including:
   a handle with a lumen extending therethrough for receiving the guide wire which allows the handle to be directly mountable on the guide wire,
   means associated with the handle for locking the guide wire to the torque handle to allow the user to rotate the guide wire,
   a side port adapted to receive the proximal end of the sheath which allows a portion of the guide wire to shear the sheath from the guide wire through retraction of the sheath through the side port; and
   an extension arm extending from the handle which includes a distal end having an opening adapted to receive both the guide wire and the sheath, the end of the extension arm being disposed longitudinally away from the side port.

2. The embolic filtering system of claim 1, wherein the sheath includes a split seam extending therethrough from the proximal end to a location proximal to the distal end portion to enhance the ability of the sheath to shear as the sheath is retracted through the side port.

3. The embolic filtering system of claim 1, further including a tubular member extending distally from the distal end of the extension arm which includes a lumen aligned with and in communication with the opening of the distal end that is adapted to receive the guide wire and sheath.

4. The embolic filtering system of claim 1, wherein the side port is located at an offset location from the axis defined by the guide wire.

5. The embolic filtering system of claim 1, wherein the means for locking the handle to the guide wire is attached to the handle.

6. The embolic filtering system of claim 5, wherein the extension arm is integrally formed with the means for locking the handle to the guide wire.

7. The embolic filtering system of claim 1, wherein the extension arm is removable attached to the handle.

8. The embolic filtering system of claim 1, wherein the locking means of the torque device includes a collet associated with the handle which applies force on the guide wire to lock it to the handle.

9. A torque device for rotating a guide wire and effecting the splitting of a sheath which is co-axially disposed over the guide wire, the torque device comprising:
   a handle having a lumen extending therethrough for receiving the guide wire;
   means associated with the handle to lock the guide wire within the lumen of the handle; and
   a side port adapted to receive the proximal end of the sheath which allows a portion of the guide wire to shear the sheath from the guide wire through proximal retraction of the sheath through the side port.

10. The torque device of claim 9, wherein the sheath includes a split seam extending therethrough from the proximal end to a location proximal to the distal end portion to cause the sheath to shear as the sheath is pulled through the side port.

11. The torque device of claim 9, wherein the torque device includes an extension arm extending from the handle which includes a distal end having an opening adapted to receive both the guide wire and the sheath, the distal end of the extension arm being disposed longitudinally away from the side port.

12. The torque device of claim 11, further including a tubular member extending distally from the distal end of the extension arm which includes a lumen aligned with and in communication with the opening of the distal end that is adapted to receive the guide wire and sheath.

13. The torque device of claim 11, wherein the opening of the distal end of the extension arm is aligned with the lumen of the handle.

14. The torque device of claim 11, wherein the side port is aligned offset from the opening of the distal end of the extension arm.

15. The torque device of claim 9, wherein the torque device includes a distal tubular member attached to and extending from the handle having a lumen aligned with and in communication with the lumen of the handle, the distal tubular member being adapted to receive the guide wire and sheath, the side port of the torque device being attached to the distal tubular member.

16. The torque device of claim 9, wherein the locking means includes a collet associated with the handle which applies force on the guide wire to lock it to the handle.

17. An embolic filtering system used to capture embolic debris in a body vessel, comprising:
    a guide wire;
    a filter device disposed on the guide wire;
    a sheath having a distal end portion and a proximal end, the distal end portion of the sheath being adapted to receive and maintain the filter device in an unexpanded position and removable from the filter device, the sheath having a guide wire lumen for receiving the guide wire; and
    a torque device having a handle portion directly mountable on the guide wire to allow the user to rotate the guide wire, the handle having a lumen extending therethrough for receiving the guide wire, the torque device having a side port adapted to receive the proximal end of the sheath which allows a portion of the guide wire to shear the sheath from the guide wire by the retraction of the sheath through the side port.

18. The embolic filtering system of claim 17, wherein at least a portion of the sheath includes a split seam extending therethrough to enhance the ability of the sheath to shear as the sheath is retracted through the side port.

19. The embolic filtering system of claim 17, wherein at least a portion of the wall of the sheath has reduced thickness to enhance the ability of the sheath to shear as the sheath is retracted through the side port.

20. The embolic filtering system of claim 17, wherein the torque device includes:
    a locking mechanism associated with the handle for locking the guide wire within the lumen of the handle; and
    the side port is located at an offset position from the lumen which receives the guide wire.

21. The embolic filtering system of claim 17, wherein the side port has a funnel shaped opening.

22. The embolic filtering system of claim 17, wherein the torque device includes a component to prevent the guide wire from kinking as the sheath is retracted through the side port.

23. The embolic filtering system of claim 17, wherein the locking means of the torque device includes a collet associated with the handle which applies force on the guide wire to lock it to the handle.

24. An embolic filtering system used to capture embolic debris in a body vessel, comprising:
    a guide wire;
    a filter device disposed on the guide wire;
    a sheath having a distal end portion and a proximal end, the distal end portion of the sheath being adapted to receive and maintain the filter device in an unexpanded position and removable from the filter device, the sheath having a guide wire lumen for receiving the guide wire; and
    a torque device having a handle portion directly mountable on the guide, the handle having a lumen extending therethrough for receiving the guide wire and a locking mechanism for locking the torque device to the guide wire, a second lumen formed on the handle separate and offset from the guide wire receiving lumen which allows a portion of the guide wire to shear the sheath away from the guide wire by the retraction of the sheath through the second lumen.

* * * * *